US008105615B2

(12) United States Patent
Varadhachary et al.

(10) Patent No.: US 8,105,615 B2
(45) Date of Patent: *Jan. 31, 2012

(54) LACTOFERRIN AS AN ADJUVANT IN CANCER VACCINES

(75) Inventors: Atul Varadhachary, Houston, TX (US); Federica Pericle, Houston, TX (US)

(73) Assignee: Agennix Incorporated, Houston, TX (US)

( * ) Notice: Subject to any disclaimer, the term of this patent is extended or adjusted under 35 U.S.C. 154(b) by 1563 days.

This patent is subject to a terminal disclaimer.

(21) Appl. No.: 10/862,213

(22) Filed: Jun. 7, 2004

(65) Prior Publication Data

US 2005/0019342 A1 Jan. 27, 2005

Related U.S. Application Data

(60) Provisional application No. 60/476,318, filed on Jun. 6, 2003, provisional application No. 60/498,236, filed on Aug. 27, 2003.

(51) Int. Cl.
A61K 39/00 (2006.01)
A61K 39/39 (2006.01)
A61K 38/00 (2006.01)
A61K 38/17 (2006.01)

(52) U.S. Cl. .............. 424/277.1; 424/278.1; 514/5.4; 514/19.3; 514/19.4; 514/21.1

(58) Field of Classification Search .............. None
See application file for complete search history.

(56) References Cited

U.S. PATENT DOCUMENTS

| 4,791,193 | A | * | 12/1988 | Okonogi et al. ............. 530/416 |
|---|---|---|---|---|
| 4,977,137 | A | | 12/1990 | Nichols et al. |
| 5,006,333 | A | | 4/1991 | Saifer et al. |
| 5,198,419 | A | | 3/1993 | Ando et al. |
| 5,466,669 | A | * | 11/1995 | Konig et al. .................... 514/12 |
| 5,571,691 | A | | 11/1996 | Conneely et al. |
| 5,571,697 | A | | 11/1996 | Conneely et al. |
| 5,571,896 | A | | 11/1996 | Conneely et al. |
| 5,712,247 | A | | 1/1998 | Wu et al. |
| 5,766,939 | A | | 6/1998 | Conneely et al. |
| 5,833,975 | A | | 11/1998 | Paoletti et al. ................ 424/93.2 |
| 5,849,881 | A | | 12/1998 | Conneely et al. |
| 5,919,913 | A | | 7/1999 | Nuyens et al. |
| 5,955,316 | A | | 9/1999 | Conneely et al. |
| 6,066,469 | A | | 5/2000 | Kruzel et al. |
| 6,080,559 | A | | 6/2000 | Conneely et al. |
| 6,100,054 | A | | 8/2000 | Conneely et al. |
| 6,111,081 | A | | 8/2000 | Conneely et al. |
| 6,228,614 | B1 | | 5/2001 | Conneely et al. |
| 6,277,817 | B1 | | 8/2001 | Kruzel et al. |
| 6,333,311 | B1 | | 12/2001 | Nuijens et al. |
| 6,399,570 | B1 | | 6/2002 | Mann et al. |
| 6,455,687 | B1 | | 9/2002 | Kruzel et al. |
| 6,635,447 | B1 | | 10/2003 | Conneely et al. |
| 6,890,902 | B2 | | 5/2005 | Svendsen et al. ............. 514/12 |
| 7,026,295 | B2 | | 4/2006 | Varadhachary et al. ........ 514/12 |
| 7,034,126 | B2 | | 4/2006 | Engelmayer et al. ............ 514/6 |
| 7,323,443 | B2 | | 1/2008 | Varadhachary et al. .......... 514/6 |
| 7,592,306 | B2 | | 9/2009 | Varadhachary et al. .......... 514/6 |
| 2001/0007659 | A1 | * | 7/2001 | Wong-Staal et al. ....... 424/93.21 |
| 2001/0036928 | A1 | * | 11/2001 | Chamberlain et al. .......... 514/44 |
| 2002/0016289 | A1 | | 2/2002 | Conneely et al. |
| 2002/0072596 | A1 | | 6/2002 | Ruben et al. |
| 2002/0198362 | A1 | * | 12/2002 | Gaiger et al. .................. 530/350 |
| 2003/0022821 | A1 | | 1/2003 | Svenden et al. ................. 514/12 |
| 2003/0096736 | A1 | | 5/2003 | Kruzel et al. .................. 514/179 |
| 2003/0105006 | A1 | | 6/2003 | Mann et al. |
| 2003/0190303 | A1 | | 10/2003 | Kimber et al. |
| 2003/0203839 | A1 | | 10/2003 | Kruzel et al. |
| 2004/0009895 | A1 | | 1/2004 | Varadhachary et al. |
| 2004/0009896 | A1 | | 1/2004 | Glynn et al. |
| 2004/0023334 | A1 | | 2/2004 | Prior |
| 2004/0082504 | A1 | | 4/2004 | Varadhachary et al. |
| 2004/0142037 | A1 | | 7/2004 | Engelmayer et al. |
| 2004/0151784 | A1 | | 8/2004 | Varadhachary et al. |
| 2004/0152623 | A1 | | 8/2004 | Varadhachary et al. |
| 2004/0152624 | A1 | | 8/2004 | Varadhachary et al. |
| 2004/0176276 | A1 | | 9/2004 | Varadhachary et al. |
| 2005/0004006 | A1 | | 1/2005 | Engelmayer et al. |
| 2005/0019342 | A1 | | 1/2005 | Varadhachary et al. |
| 2005/0064546 | A1 | | 3/2005 | Conneely et al. |
| 2005/0075277 | A1 | | 4/2005 | Varadhachary et al. |
| 2010/0137208 | A1 | | 6/2010 | Varadhachary et al. ........ 514/12 |

FOREIGN PATENT DOCUMENTS

| EP | 0 730 868 | 9/1996 |
|---|---|---|
| JP | 63-051337 | 3/1988 |
| JP | 05-186368 | 7/1993 |
| JP | 07-179355 | 7/1995 |
| JP | 09-194338 | 7/1997 |
| JP | 10-059864 | 3/1998 |
| JP | 2000-229881 | 8/2000 |
| JP | 2001-504447 | 3/2001 |
| JP | 2002-519332 | 7/2002 |
| JP | 2002-525028 | 8/2002 |
| JP | 2002-535004 T | 10/2002 |
| JP | 2003-512048 | 4/2003 |
| JP | 2007-233064 | 9/2007 |

(Continued)

OTHER PUBLICATIONS

Verma et al (Nature, 1997, vol. 389, pp. 239-242).*
Eck et al (Gene-Based Therapy, In: The Pharmacological Basis of Therapeutics, Goodman and Gilman, Ed.s, 1996, pp. 77-101).*
Orkin ("Report and Recommendation of the Panel to Assess the NIH Investment in Research on Gene Therapy", NIH, 1995).*
The abstract of Wheeler (Salud p'ublica de M'exico, (Jul.-Aug. 1997) 39 (4) 283-7).*
Efferson et al (Anticancer research, 2005, vol. 25, pp. 715-24).*
Bachman et al (Journal of Immunology, 2005, vol. 175, pp. 4677-4685).*
Kruzel and Zimecki (Archivum Immunologine Therapiae Experimentalis, 2002, vol. 50, pp. 399-410).*
Zimecki and Kruzel (Immunology Letters, 2000, vol. 74, pp. 183-188).*

(Continued)

Primary Examiner — Karen Canella
(74) Attorney, Agent, or Firm — Fulbright & Jaworski L.L.P.

(57) ABSTRACT

The present invention relates to methods of treating cancer by administering a composition of lactoferrin (LF) in combination with cancer vaccines.

4 Claims, 5 Drawing Sheets

FOREIGN PATENT DOCUMENTS

| WO | WO 98/06425 | | 2/1998 |
|---|---|---|---|
| WO | WO 98/33509 | | 8/1998 |
| WO | WO 98/44940 | | 10/1998 |
| WO | WO-9952545 | A1 | 10/1999 |
| WO | 00/44899 | A1 | 8/2000 |
| WO | WO 01/78777 | * | 10/2001 |
| WO | WO-02/03910 | | 1/2002 |
| WO | WO 2006/054908 | | 5/2006 |
| WO | WO 2008/079030 | | 7/2008 |

OTHER PUBLICATIONS

Nichols et al (Clin Exp Immunol, 1993, vol. 94, pp. 4-10.*
Lau et al (Journal of Immunotherapy, Jan.-Feb. 2001, 24(1):66-78).*
Marshall et al (Journal of Clinical Oncology, 2000, vol. 18, pp. 3964-3973).*
Wang et al (Clinical Cancer Research, vol. 5, pp. 2756-2765).*
Roitt et al (Immunology (textbook), 1998, pp. 232 and 270).*
M. Zimecki and M. Machnicki. Lactoferrin inhibits the effector phase of the delayed type hypersensitivity to sheep erythrocytes. *Arch Immunol Ther Exp* (Warsz). 1994;42(3)171-7.
Harms JS et al. Regulation of transgene expression in genetic immunization. Braz J Med Bio Res. Feb. 1999;32(2):155-62.
Liu MA. DNA vaccines: a review. J Inter Med. Apr. 2003;253(4):402-10. (Review).
Norman JA et al. Development of improved vectors for DNA-based immunization and other gene therapy applications. Vaccine. Jun. 1997;15(8):801-3.
Rovero et al. DNA vaccination against rat her-2/neu p185 more effectively inhibits carcinogenesis than transplantable carcinomas in transgenic BALB/c mice. J Immunol. 2000;165(9):5133.
Actor et al., "Lactoferrin immunomodulation of DTH response in mice"; Int Immunopharmacol. Mar. 2002;2(4):475-86.
Dvorak et al., "Experimental design for vaccine preparations against human malignant tumors"; Med Hypotheses. Aug. 1986;20(4):429-52.
International Preliminary Report on Patentability issued Mar. 1, 2008 (published Jun. 13, 2008) during the prosecution of International Application No. PCT/US04/17933.
International Search Report issued Nov. 23, 2007 (published Jan. 17, 2008) during the prosecution of International Application No. PCT/US04/17933.
Supplementary European Search Report issued Aug. 21, 2009 (published Aug. 28, 2009) during the prosecution of European Application No. 04 81 7695.
Written Opinion issued Nov. 23, 2007 (published Dec. 7, 2007) during the prosecution of International Application No. PCT/US04/17933.
Disis, M.L., et al; "Delayed-Type Hypersensitivity Response Is a Predict or of Peripheral Blood T-Cell Immunity After HER-2/neu Peptide Immunization", Clin. Cancer Res. 2000, vol. 6(4), pp. 1347-1350.
Fisk, B., et al; "Identification of an Immunodominant Peptide of HER-2/neu Protooncogene Recognized by Ovarian Tumor-Specific Cytotoxic T Lymphocyte Lines", J. Exp. Med., 1995, vol. 181(6), pp. 2109-2117.
Ioannides, C.G., et al.; "Cytotoxic T Cells Isolated From Ovarian Malignant Ascites Recognize a Peptide Derived From the HER-2/neu Proto-Oncogene", Cell Immunol, 1993, vol. 151(1), pp. 225-234.
Peoples, G.E., et al.; "T Lymphocytes that Infiltrate Tumors and Atherosclerotic Plaques Produce Heparin-Binding Epidermal Growth Factor-Like Growth Factor and Basic Fibroblast Growth Factor: A Potential Pathologic Role", Proc. Nat'l Acad. Sci. USA, 1995, vol. 92(14), pp. 6547-6551.
Japanese Office Action, issued May 26, 2010 (published May 26, 2010) during the prosecution of Japanese Application No. 2006-533575.
Dredge et al., "Adjuvants and the promotion of Th1-type cytokines in tumour immunotherapy," *Cancer Immunol. Immunother.*, 51(10): 521-31, 2002.
Dudley et al., "Cancer regression and autoimmunity in patients after clonal repopulation with antitumor lymphocytes," *Science*, 298(5594): 850-4, 2002.

Kocieba et al., "The adjuvant activity of lactoferrin in the generation of DTH to ovalbumin can be inhibited by bovine serum albumin bearing alpha-D-mannopyranosyl residues," *Cell Mol. Biol. Lett.*, 7(4): 1131-6, 2002.
Kruzel et al., "Lactoferrin and immunologic dissonance: clinical implications," *Arch. Immunol. Ther. Exp. (Warsz)*, 50(6): 399-410, 2002.
Mayer et al., "CT number distribution and its association with local control and as a marker of lung tumor response to radiation," *Radiat. Oncol. Investig.*, 6(6): 281-8, 1998.
Ohara et al., "Radioresponse to thymomas verified with histologic response," *Acta Oncol.*, 37(5): 471-4, 1998.
Wolf et al., "Lactoferrin inhibits growth of malignant tumors of the head and neck," *ORL J. Otorhinolaryngol. Relat. Spec.*, 65(5): 245-9, 2003.
Zimecki et al., "Systemic or local co-administration of lactoferrin with sensitizing dose of antigen enhances delayed type hypersensitivity in mice," *Immunol. Lett.*, 74(3): 183-8, 2000.
Cusi et al., "Intranasal immunization with mumps virus DNA vaccine delivered by influenza virosomes elicits mucosal and systemic immunity," *Virology*, 277(1): 111-118.
English Translation of Office Communication issued in Japanese Patent Application No. 2006533575, dated Aug. 25, 2011.
Etchart et al, "Class I-restricted CTL induction by mucosal immunization with naked DNA encoding measles virus haemagglutinin," *J. Gen. Virol.*, 78 (Pt. 7): 1577-1580, 1997.
Masaaki et al., "Metastasis suppression by lactoferrin, activation of caspase-1 and growth of IL-18 in small intestinal epithelial cells," Collected Abstract, Annual Meeting of the Pharmaceutical Society of Japan, 123(3):102, 2003.
Amouric et al, "Effect of Lactoferrin on the Growth of a Human Colon Adenocarcinoma Cell Line —Comparison with Transferrin" in Vitro vol. 20 No. 7, Jul. 1984, pp. 543-548.
Atkins Cytokine-based therapy and biochemotherapy for advanced melanoma, Clin Cancer Res, Apr 1, 2006;12(7 Pt 2):2353s-2358s. Review.
Bajetta et al., Multicenter phase III randomized trial of polychemotherapy (CVD regimen) versus the same chemotherapy (CT) plus subcutaneous interleukin-2 and interferon-alpha2b in metastatic melanoma, Ann Oncol. Apr. 2006;17(4):571-7. Epub 2006 Feb 9.
Barresi et al, "Lactoferrin in Benign Hypertrophy and Carcinomas of the Prostatic Gland," Virchows Archiv (Pathol Ant) 403; 1984, pp. 59-66.
Becerra eta I., Increased toxicity and lack of efficacy of Rofecoxib in combination with chemotherapy for treatment of metastatic colorectal cancer: A phase II study, Int. J. Cancer: 105, 868-872 [2003].
Beyer and Schultze, "Regulatory T cells in cancer." Blood. Aug 1, 2006;108(3):804-11.
Bezault et al, "Human Lactoferrin Inhibits Growth of Solid Tumors and Development of Experimental Metastases in Mice," Cancer Research 54, May 1, 1994, pp. 2310-2312.
Brinkman et a; Use or selenium in chemoprevention of bladder cancer. Lancet Oncol. Sep. 2006;7(9):766-74, Review.
Brock et al, "Interaction of Lactoferrin with Mononuclear and Colon Carcinoma cells," Lactoferrin—Structure and Function, T.W. Hutches, S.V. Rumball and B. Lonnerdal. New York, Plenum PRess: pp. 157-169. (1994).
Bronte, "Genetic vaccination for the active immunotherapy of cancer," *Current Gene Therapy*, 1:53-100, 2001.
Bruserud and Wendelboe, Biological treatment in acute myelogenous leukaemia: how should T-cell targeting immunotherapy be combined with intensive chemotherapy? Expert Opin Biol Ther. Nov. 2001;1(6):1005-16.
Cameron et al. Temporal progression of metastasis in lung: cell survival, dormancy, and location dependence of metastatic inefficiency. Cancer Res. May 1, 2000;60(9):2541-6.
Costanzi et al., Combination chemotherapy plus levamisole in the treatment of disseminated malignant melanoma. A Southwest Oncology Group study. Cancer. Feb. 15, 1984;53(4):833-6.
Cumulative list of Designated and or Approved Orphan Products, Effective: May 16, 2008, http://www.fda.gov/orphan/disgnat/list.xls.

Curcio et al., Nonredundant roles of antibody, cytokines, and perforin in the eradication of established Her-2/neu carcinomas. J Clin Invest. Apr. 2003;111(8):1161-70.

Damiens et al, "Effects of Human Lactoferrin on NK Cell Cytotoxicity Against Haematopoietic and Epithelial Tumour Cells," Biochimica et Biophysica Acta 1402, 1998, pp. 277-287.

Damiens et al, "Lactoferrin Inhibits G1 Cyclin-Dependent Kinases During Growth Arrest of Human Breast Carcinoma Cells," Journal of Cellular Biochemistry 72, 1999, pp. 486-498.

De Gast et al., Reinfusion of autologous lymphocytes with granulocyte-macrophage colony-stimulating factor induces rapid recovery of CD4+ and CD8+ T cells after high-dose chemotherapy for metastatic breast cancer. J Clin Oncol. Jan 1, 2002;20(1):58-64.

Decision on Appeal 2008-3921 issued in U.S. Appl. No. 10/732,429, decided Mar. 5, 2009.

Decker et al., "A retrogen plasmid-based vaccine generates high titer antibody responses against the autologous cancer antigen surviving and demonstrates anti-tumor efficacy," *Cancer Letters*, 237(1):45-55, 2006.

Dela Cruz et al., "Protein vaccination with the HER2/neu extracellular domain plus anti-HER2/neu antibody-cytokine fusion proteins induces a protective anti-HER2/neu immune response in mice," *Vaccine*, 21(13-14):1317-1326, 2003.

Donnelly et al., "DNA vaccines: progress and challenges," *The Journal of Immunology*, 175:633-639, 2005.

Early Breast Cancer Trialists' Collaborative Group. "Effects of chemotherapy and hormonal therapy for early breast cancer on recurrence and 15-year survival: an overview of the randomised trials." Lancet. May 14-20 2005;365(9472):1687-1717.

Escudier et al., Randomized Phase III trial of the Raf kinase and VEGFR inhibitor sorafenib (BAY 43-9006) in patients with advanced renal cell carcinoma (RCC). Proceedings from the 2005 annual meeting of the American Society of Clinical Oncology (ASCO). Abstract #LBA4510.

FDA correspondence regarding IND 11728, Feb. 28, 2006.

Fields et al., "Radiosensitization produced in vivo by once- vs. twice-weekly 2'2'-difluoro-2'- deoxycytidine (gemcitabine)," *Int J Radiat Oncol Biol Phys.*, 47(3):785-791, 2000.

Fujita et al, "Down-Regulation of 2-Amino-3, 8-dimethylimidazo [4,5-f] Quinoxaline (MeIQx)- induced CYP1A2 Expression is Associated with Bovine Lactoferrin Inhibition of MeIQx-induced Liver and Colon Carcinogenesis in Rats," Jpn. J. Cancer Res. 93, Jun. 2002, pp. 616-625.

Gelber et al., "Adjuvant chemotherapy plus tamoxifen compared with tamoxifen alone for postmenopausal breast cancer: meta-analysis of quality-adjusted survival," Lancet., Apr. 20, 1996;347(9008):1066-71).

Gordon et al., "The treatment of psoriasis and psoriatic arthritis: an interdisciplinary approach," *J. Am. Acad. Dermatol.*, 54(3):S85-S91, 2006.

Grande et al., "Interleukin-2 for the treatment of solid tumors other than melanoma and renal cell carcinoma," Anticancer Drugs, 17(1):1-12, 2006.

Griffiths et al., "Exogenous topical lactoferrin inhibits allergen-induced Langerhans cell migration and cutaneous inflammation in humans," *British Journal of Dermatology*, 144:715725, 2001.

Gustalla et al., "The taxanes: toxicity and quality of life considerations in advanced ovarian cancer," *British Journal of Cancer*, 89:S16-S22, 2003.

Hayes et al., Phase I trial of oral talactoferrin alfa in refractory solid tumors. Investigational New Drugs, 2006;24(3):233-40.

Hayes et at, "Phase IB trial of oral talactoferrin in the treatment of patients with metastatic solid tumors," Investigational New Drugs, 2009.

Herberman, "Cancer immunotherapy with natural killer cells." Semin Oncol. 2002 Jun;29(3 Suppl 7):27-30.

Hung and Lau, "Basic science of HER-2/neu: a review," *Semin. Oncol.*, 26(4 Suppl. 12):51-59, 1999.

Ibragimova and Wade, "Stability of the β-sheet of the WW domain: a molecular dynamics simulation study," *Biophysical Journal*, 77:2191-2198, 1999.

Iigo et al, "Inhibitory Effects of Bovine Lactoferrin on Colon Carcinoma 26 Lung Metastasis in Mice," Clinical & experimental Metastasis 17, 1999, pp. 35-40.

Ilgo et al., "Fluctuation of cytokine in mucosa of small intestine and T-cell by lactoferrin," Summaries of the Annual Meeting of the Pharmaceutical Society of Japan, English Abstract, 121(3):29, 2001.

Inaba et al., "Granulocytes, macrophages, and dendritic cells arise from a common major histocompatibility complex class II-negative progenitor in mouse bone marrow," *Proc. Natl. Acad. Sci. USA*, 90:3038-3042, 1993.

Jaiyesimi et al., Use of tamoxifen for breast cancer: twenty-eight years later, J Clin Oncol., Feb.1995 ;13(2):513-29.

Jonasch et al., "Phase 2 trial of talactoferrin in previously treated patients with metastatic renal cell carcinoma," Cancer, 113(1):72-77, 2008.

Kageshita et al., "Down-regulation of HLA class I antigen-processing molecules in malignant melanoma: association with disease progression." Am J Pathol. Mar. 1999;154(3):745-54.

Kelloff et al., AACR Task Force on Cancer Prevention., Progress in chemoprevention drug development: the promise of molecular biotmarkers for prevention of intraepithelial neoplasia and cancer—a plan to move forward, Clin Cancer Res., Jun. 15, 2006; 12(12):3661-97.

Kerbel, "Human Tumor Xenografts as Predictive Preclinical Models for Anticancer Drug Activity in Humans," *Cancer Biology & Therapy*, 2(4Suppl.1):S134-S139, 2003.

Kim et al., "Tumor-driven evolution of immunosuppressive networks during malignant progression," Cancer Res. Jun. 1, 2006;66(11):5527-36.

Kobie et al., "Transforming growth factor beta inhibits the antigen-presenting functions and antitumor activity of dendritic cell vaccines." Cancer Res. Apr. 15, 2003;63(8):1860-4.

Kramer and Brown, Should tamoxifen be used in breast cancer prevention? Drug Saf. 2004;27(13):979-89.

Krzakowski, "New agents within the preoperative chemotherapy of non-small cell lung cancer," *Lung Cancer*, 34:S159-S163, 2001.

Kuhara et al., "Orally Administered Lactoferrin Exerts an Antimetastatic Effect and Enhances Production of IL-18 in the Intestinal Epithelium," *Nutrition and Cancer*, 38(2):192-199, 2000.

Kuhara, "Induced IL-18 production from intestinal epithelium by lactoferrin and significance thereof," *Clinical Immunology*, English Abstract, 34(3):376-381, 2000.

Lebwohl et al., "Clinical development of platinum complexes in cancer therapy: an historical perspective and an update," *European Journal of Cancer*, 34(10):1522-1534, 1998.

Lee, "Protein drug oral delivery: the recent progress," *Arch Pharm Res.*, 25(5):572-584, 2002.

Lens et al., Use of tamoxifen in the treatment of malignant melanoma. Cancer. Abstract, 2003 Oct 1;98(7):1355-61. Review.

Letter and Application to Food and Drug Administration, Office of Orphan Products Development and from Agennix, Inc., in support of orphan drug designation request #03-1822, for recombinant human lactoferrin for the treatment of renal cell carcinoma, filed Jul. 11, 2006.

Letter and Application to Food and Drug Administration, Office of Orphan Products Development, from Agennix, Inc., in support of orphan drug designation request #07-2367, for talactoferrin alfa for the treatment of stage III/IV non-small cell lung cancer, filed Dec. 29, 2006.

Letter to Agennix, Inc. and from Food and Drug Administration, Office of Orphan Products Development, letter of approval of orphan drug designation request #03-1822, mailed Sep. 29, 2006.

Letter to Agennix, Inc. and from Food and Drug Administration, Office of Orphan Products Development, letter of approval of orphan drug designation request #07-2367, mailed Aug. 8, 2007.

Letter to Agennix, Inc. and from Food and Drug Administration, Receipt of IND application BB-IND #11728, Jun. 7, 2004.

Letter to Food and Drug Administration, Office of Orphan Drug Products Development and from Agennix, Inc., in support of orphan drug designation request #07-2367, for talactoferrin alfa in stage III/IV non-small cell lung cancer, filed May 18, 2007.

Letter to Food and Drug Administration, Office of Orphan Products Development and from Agennix, Inc., in support of orphan drug designation request #03-1822, for recombinant human lactoferrin for treatment of renal cell carcinoma, filed Sep. 8, 2006.

Lissoni et al., A randomized study of immunotherapy with low-dose subcutaneous interleukin-2 plus melatonin vs chemotherapy with cisplatin and etoposide as first-line therapy for advanced non-small cell lung cancer. Tumori. Dec 31, 1994;80(6):464-7.

Loughlin et al, "The relationship of lactoferrin to the anemia of renal cell carcinoma," *Can.*, Abstract only, 59(3):566-571, 1987.

Masuda et al, "Chemopreventive Effects of Bovine Lactoferrin on N-Butyl-N (4-hydroxybutyl) Nitrosamine-Induced Rat Bladder Carcinogenesis," Jpn. J. Cancer Res. 91, Jun. 2000, pp. 582-588.

McColl, "Pharmacological therapies for the treatment of osteoarthritis," *Med. J. Aust.*, 175:S108-S111, 2001.

Mojaverian et al., "Single and Multiple Dose Safety, Tolerability and Pharmacokinetics (PK) of Oral Recombinant Lactoferrin (rhLF) in Healthy Subjects," *Proceedings of the annual meeting of the American Association of Pharmaceutical Scientists*, 2003.

Mok and Leung, Changes in chemotherapy for pancreatic cancer. Hong Kong Med J. 1999 Dec;5(4):367-374.

Motzer et al., Prognostic Factors for Survival in Previously Treated Patients with Metastatic Renal Cell Carcinoma. J of Clin Oncology. 2004 Feb 3; 22(3):454-63.

National Cancer Institute websiste, "NCI Issues Clinical Announcement for Preferred Method of Treatment for Advanced Ovarian Cancer: Questions and Answers," located at http://www.cancer.gov/newscenter/pressreleases/IPchemotherapyQandA, printed Apr. 10, 2008.

National Cancer Institute website, "Radiation Therapy for Cancer: Questions and Answers," located at http://www.cancer.gov/cancertopics/factsheet/Therapy/radiation, printed Apr. 10, 2008.

Noda et al., "Inhibition of N-linked glycosylation by tunicamycin enhances sensitivity to cisplatin in human head-and-neck carcinoma cells," *Int J Cancer.*, 80(2):279-284, 1999.

Norrby et al, "Orally Administered Bovine Lactoferrin Systemically Inhibits VEGF 165 -Mediated Angiogenesis in the Rat," Int. j. Cancer 91, 2001, pp. 236-240.

Nowak et al., Combined chemoimmunotherapy of solid tumours: Improving vaccines? Adv Drug Deliv Rev. 2006 Aug 15; [Epub ahead of print].

Nowak et al., Gemcitabine exerts a selective effect on the humoral immune response: implications for combination chemo-immunotherapy. Cancer Res. Apr. 15, 2002;62(8):2353-8.

Nowak et al., Tamoxifen for hepatocellular carcinoma. Cochrane Database Syst Rev. 2004;(3):CD001024. Review.

Nowak et al., Use of tamoxifen in advanced-stage hepatocellular carcinoma. A systematic review. Cancer. Apr 1, 2005;103(7):1408-14.

Office Action issued in European Application No. 04817695.2, mailed Aug. 28, 2009.

Office Action issued in Indian Application No. 3448/DELNP/2004, mailed Jul. 12, 2010.

Office Action issued in Japanese Application No. 2004-506847, mailed Jan. 23, 2009 (English language translation).

Office Action issued in Japanese Application No. 2004-506847, mailed Jul. 30, 2010 (English language translation).

Office Action issued in U.S. Appl. No. 10/434,769, mailed Dec. 2, 2009.

Office Action issued in U.S. Appl. No. 10/434,769, mailed Feb. 9, 2007.

Office Action issued in U.S. Appl. No. 10/434,769, mailed Jul. 14, 2010.

Office Action issued in U.S. Appl. No. 10/434,769, mailed Jun. 15, 2006.

Office Action issued in U.S. Appl. No. 10/434,769, mailed Jul. 2, 2008.

Office Action issued in U.S. Appl. No. 10/434,769, mailed Mar. 23, 2006.

Office Action issued in U.S. Appl. No. 10/434,769, mailed Mar. 23, 2009.

Office Action issued in U.S. Appl. No. 10/434,769, mailed Oct. 15, 2007.

Office Action issued in U.S. Appl. No. 12/555,296, mailed Jul. 7, 2011.

Ogura et al., "Interleukin-18 stimulates hematopoietic cytokine and growth factor formation and augments circulating granulocytes in mice," *Blood*, 98(7):2101-2107, 2001.

Ohmuma, "Combination of chemotherapy and immunotherapy in man—review," Gan to Kagaku Ryoho. Aug. 1990;17(8 Pt 1):1428-36.

Oldham, "Developmental therapeutics and the design of clinical trials," in: Principles of Cancer Biotherapy, 4*th* edition, ed. Robert K. Oldham, pp. 45-58, 2003.

Osaki et al., IFN—Inducing Factor/IL-18 Administration Mediates IFN-- and IL-12-Independent Antitumor Effects, the Journal of Immunology, 1998, 160: 1742-1749.

Osterborg et al., Idiotype immunity (natural and vaccine-induced) in early stage multiple myeloma. Acta Oncol. 2000;39(7):797-800.

PCT International Preliminary Examination Report issued in International Application No. PCT/US03/14789, completed Jan. 14, 2005.

PCT International Search Report issued in International Application No. PCT/US03/14789, mailed Oct. 24, 2003.

Ridolfi et al., Italian Melanoma Intergroup. Cisplatin, dacarbazine with or without subcutaneous interleukin-2, and interferon alpha-2b in advanced melanoma outpatients: results from an Italian multicenter phase III randomized clinical trial. J Clin Oncol. Mar. 15, 2002;20(6):1600-7.

Ritchie et al., (2000) Dendritic cell elimination as an assay of cytotoxic T lymphocyte activity in vivo. J Immunol Methods 246: 109-17.

Robinson et al., Combined-modality treatment of inoperable lung cancer (i.v. immunotherapy, chemotherapy, and radiotherapy). Cancer Treat Rep. Mar. 1985;69(3):251-8.

Rosenberg et al., "Experience with the use of high-dose interleukin-2 in the treatment of 652 cancer patients," *Ann Surg.*, 210(4):474-484, 1989.

RxList Inc. website, Drug Description of Alimta®, Google cache of http://www.rxlist.com/cgi/generic/alimta.htm as retrieved on Jun. 26, 2008, printed on Jun. 29, 2008.

Sakamoto, "Establishment of human pancreas cancer cell line (SPA), iron-binding glycoproteins, antiproliferative activity of human lactoferrin," *Cancer and Chemotherapy*, English Abstract, 258(10):1557-1563, 1998.

Sakamoto, N., "Antitumor Effect of Human Lactoferrin against Newly Establishes Human Pancreatic Cancer Cell Line SPA," Gan to Kagaku Ryoho, Aug. 1998 25(10), pp. 1557-63.

Schütt et al., Immune parameters in multiple myeloma patients: influence of treatment and correlation with opportunistic infections. Leuk Lymphoma. Aug. 2006;47(8):1570-82.

Sekine et al, "Inhibition of Azoxymethane-initiated Colon Tumor by Bovine Lactoferrin Administration in F344 Rats," Jpn. J. Cancer Res. 88, Jun. 1997, pp. 523-526.

Sekine et al., Inhibition of initiation and early stage development of aberrant crypt foci and enhanced natural killer activity in male rats administered bovine Lactoferrin concomitantly with azoxymethane. Cancer Lett. Dec. 23, 1997;121(2):211-6.

Shau et al., "Modulation of Natural Killer and Lymphokine-activated Killer Cell Cytotoxicity by Lactoferrin," Journal of Leukocyte Biology vol. 51, Apr. 1992, pp. 343-349.

Siefker-Radtke et al., Phase III trial of fluorouracil, interferon alpha-2b, and cisplatin versus methotrexate, vinblastine, doxorubicin, and cisplatin in metastatic or unresectable urothelial cancer. J Clin Oncol. Mar. 1, 2002;20(5):1361-7.

Smith et al., "Animal models for the study of squamous cell carcinoma of the upper aerodigestive tract: a historical perspective with review of their utility and limitations. Part A. Chemically-induced de novo cancer, syngeneic animal models of HNSCC, animal models of transplanted xenogeneic human tumors," *Int J Cancer.*, 118:2111-2122, 2006.

Smith et al., Retinoids as chemoprevention for head and neck cancer: where do we go from here? Crit Rev Oncol Hematol. Aug. 2005;55(2):143-52.

Smorenburg et al., "Combination chemotherapy of the taxanes and antimetabolites: its use and limitations," *European Journal of Cancer*, 37(18):2310-2323, 2001.

Sommer et al., Evaluation of vaccine dosing in patients with solid tumors receiving myelosuppressive chemotherapy. J Oncol Pharm Pract. Sep. 2006;12(3):143-54. Leuk Lymphoma. Aug. 2006;47(8):1570-82.

Srinivas et al., "Talactoferrin alfa may prolong progression-free survival in advanced renal carcinoma patients," *Journal of Clinical Oncology*, 2006 ASCO Annual Meeting Proceedings Part I. vol. 24, No. 18S (Jun. 20 Supplement), 2006: 4600.

Steinbach et al., "The effect of celecoxib, a cyclooxygenase-2 inhibitor, in familial adenomatous polyposis," N Engl J Med. Jun. 29, 2000; 342(26):1946-52.

Szarka et al., "Chemoprevention of cancer," *Curr Probl Cancer*, 18(1):6-79, 1994.

Talmadge et al., "Murine models to evaluate novel and conventional therapeutic strategies for cancer," *Am. J. Pathol.*, 170(3):793-804, 2007.

Tanaka et al, "Bovine Lactoferrin Inhibits Rat Tongue Carcinogenesis," Elsevier Sciences B.V. Lactoferrin: Structure, Function and Applications 2000, pp. 401 - 411.

Teicher et al., "Treatment regimens including the multitargeted antifolate LY231514 in human tumor xenografts," *Clin Cancer Res.*, 6(3):1016-1023, 2000.

Teng et al., "Lactoferrin Gene: Methylation, Expression and Cancer," Elseiver Science B.V. -Lactoferrin: Structure, Function and Application, 2000, pp. 247 - 255.

Thomas and Smith, "Animal models for the study of squamous cell carcinoma of the upper aerodigestive tract: a historical perspective with review of their utility and limitations part B. Transgenic mouse models," Review, *Int J Cancer.*, 118(10):2379-2380, 2006.

Thompson et al., The influence of finasteride on the development of prostate cancer. N Engl J Med. Jul. 17, 2003;349(3):215-24. Epub Jun. 24, 2003.

Tsuda et al, "Cancer Prevention by Bovine Lactoferrin and Underlying Mechanisms—a Review of Experimental and Clinical Studies," Biochem. Cell Biol. 80, 2002, pp. 131-136.

Tsuda et al, "Milk and Dairy Products in Cancer Prevention: Focus on Bovine Lactoferrin," Elsevier Science B.V. — Mutation Research 462, 2000, pp. 227-233.

Tsuda et al., "Prevention of Carcinogenesis and Metastasis by Dietary Bovine Lactoferrin," Elsevier Sciences B.V. — Lactoferrin: Structure, Function and Applications, 2000, pp. 389-399.

Tsuda et al., "Prevention of Colon Carcinogenesis and Carcinoma Metastasis by Orally Administered Bovine Lactoferrin in animals," BioFactors 12, 2000, pp. 83-88.

Tsuda et al, "Inhibition of Azoxymethane Initiated Colon Tumor and Aberrant Crypt FOCI Development by Bovine Lactoferrin Administration in F344 Rats," Advances in Lactoferrin research, edited by Spik et al, Plenum Press, New York, 1998, pp. 273-283.

U.S. Food and Drug Administration website, "Questions and Answers about Eloxatin (oxaliplatin for injection)," located at http://www.fda.gov/cder/drug/infopage/eloxatin/default.htm, last updated Aug. 9, 2002, printed Apr. 10, 2008.

Uherek et al., Retargeting of natural killer—cell cytolytic activity to ErbB2—expressing cancer cells results in efficient and selective tumor cell destruction. Blood. Aug. 15, 2002;100(4):1265-73.

Unger et al., Estimated impact of the Prostate Cancer Prevention Trial on population mortality. Cancer. Apr. 1, 2005;103(7):1375-80.

Ushida et al, "Inhibitory Effects of Bovine Lactoferrin on Intestinal Polyposis in the Apc Mouse," Cancer Letters 134, 1998, pp. 141-145.

Ushida et al., "Possible chemopreventive effects of bovine lactoferrin on esophagus and lung carcinogenesis in the rat,"*Japn. J. Cancer Res.*, 90:262-267, 1999.

van Belzen, nico, "The Role of Lactoferrin in Cancer Prevention," Sciences Des Aliments, 22, 2002, pp. 461-468.

Van Den Broeke et al. Dendritic cell-induced activation of adaptive and innate antitumor immunity. J Immunol. 2003 Dec 1;171(11):5842-52.

Varadhachary et al., "Recombinant Human Lactoferrin, a novel oral Anti-Cancer Drug," www.asco.org, Abstract No. 934, 2003.

Varadhachary et al. Oral lactoferrin inhibits growth of established tumors and potentiates conventional chemotherapy. Int. J. Cancer, 111: 398-403., 2004.

Varadhachary et al. Oral Talactoferrin Alfa a Novel Anti-Cancer Therapy: Experimental and Clinical Experience. Invited Presentation, Second Cancer Vaccine Meeting, Siena, Dec. 2006.

Varadhachary et al., "Intratumoral Injection of human Recombinant Lactoferrin Inhibits the Growth of Human Tumors Implanted in Athymic Nude Mice," www.asco.org, Abstract No. 1875, 2002.

Voskoglou-Nomikos et al., "Clinical predictive value of the in vitro cell line, human xenograft, and mouse allograft preclinical cancer models," *Clin. Can. Res.*, 9:4227-4239, 2003.

Walter et al., "Intratumoral Chemotherapy," *Neurosurgery*, 37(6):1129-1145, 1995.

Wang et al., "Activation of Intestinal Mucosal Immunity in Tumor-bearing Mice by Lactoferrin," Jpn. J. Cancer Res. 91, Oct. 2000, pp. 1022-1027.

Wang et al., Adding oral talactoferrin to first-line NSCLC chemotherapy safely enhanced efficacy in a randomized trial. Abstract #7095, Proceedings of the American Society of Clinical Oncology, 2006.

Wang et al., RhLF NSCLC Clinical Investigator Group. Double blind, Placebo Controlled Trial of Oral Lactoferrin in Combination Therapy for First Line Non-small Cell Lung Cancer (NSCLC). Journal of Clinical Oncology, 2005 ASCO Annual Meeting Proceedings. vol. 23, No. 16S, Part I of II (Jun. 1 Supplement), 2005: 7141.

Yang et al., A randomized trial of bevacizumab, an anti–vascular endothelial growth factor antibody, for metastatic Renal Cancer. N Engl J Med. Jul. 31, 2003;349(5):427-34.

Yoo et al., "Bovine Lactoferrin and Lactoferricin Inhibit Tumor Metastasis in Mice," Advances in Lactoferrin Research, Chapter 35, Plenum Press, New York, 1998, pp. 285-291.

Yoo et al., "Bovine Lactoferrin and Lactoferricin, a Peptide Derived from Bovine Lactoferrin, Inhibit Tumor Metastasis in mice," Jpn. J. Cancer Res. 88, Feb. 1997, pp. 184-190.

Zimecki et al., "Human lactoferrin induces phenotypic and functional changes in murine splenic B cells," *Immunology*, 86:122-127, 1995.

* cited by examiner

LACTOFERRIN AS AN ADJUVANT IN CANCER VACCINES

CROSS-REFERENCE TO RELATED APPLICATIONS

This application claims priority to U.S. Provisional Application Nos. 60/476,318 filed Jun. 6, 2003 and 60/498,236 filed Aug. 27, 2003, each of which is incorporated herein by reference in its entirety.

TECHNICAL FIELD

The present invention relates to methods of treating cancer by administering a composition of lactoferrin (LF) in combination with cancer vaccines.

BACKGROUND OF THE INVENTION

Currently, there are few effective options for the treatment of many common cancer types. The course of treatment for a given individual depends on the diagnosis, the stage to which the disease has developed, and factors such as age, sex, and general health of the patient. The most conventional options of cancer treatment are surgery, radiation therapy, and chemotherapy. Surgery plays a central role in the diagnosis and treatment of cancer. Typically, a surgical approach is required for biopsy and the removal of cancerous growth. However, if the cancer has metastasized and is widespread, surgery is unlikely to result in a cure, and an alternate approach must be taken. Side effects of surgery include diminished structural or organ function and increased risk of infection, bleeding, or coagulation related complications. Radiation therapy, chemotherapy, biotherapy and immunotherapy are alternatives to surgical treatment of cancer (Mayer, 1998; Ohara. 1998; Ho et al., 1998). The disadvantage of many of the alternative therapies are the side effects, which can include myelosuppression, skin irritation, difficulty swallowing, dry mouth, nausea, diarrhea, hair loss, weight loss, and loss of energy (Curran, 1998; Brizel, 1998).

Significant progress in understanding the molecular basis of the immune response to cancer as well as increased understanding of the basic mechanisms of cellular immunology have combined to open new opportunities for the development of effective immunotherapy for patients with cancer (Dudley et al., 2002). Immunotherapy includes both innate and specific immune responses that have the potential to treat different tumor types. The activation of tumor antigen-specific T lymphocytes or non-specific macrophages and natural killer (NK) cells using immunotherapeutic approaches may lead to the destruction of tumor cells (Curiel et al., 2002). Cancer vaccines involve the induction of a specific immune response. However, the administration of a tumor antigen alone is often not sufficient to stimulate an appropriate immune response. Incorporating an immunological adjuvant into a vaccine regimen often improves anti-tumor activity (Dredge et al., 2002).

Lactoferrin is a single chain metal binding glycoprotein. Many cells types, such as monocytes, macrophages, lymphocytes, and intestinal brush-border cells, are known to have lactoferrin receptors. In addition to lactoferrin being an essential growth factor for both B and T lymphocytes, lactoferrin has a wide array of functions related to host primary defense mechanisms. For example, lactoferrin has been reported to activate natural killer (NK) cells, induce colony-stimulating activity, activate polymorphonuclear neutrophils (PMN), regulate granulopoeisis, enhance antibody-dependent cell cytotoxicity, stimulate lymphokine-activated killer (LAK) cell activity, and potentiate macrophage toxicity.

Recombinant human lactoferrin has previously been described as being purified after expression in a variety of prokaryotic and eukaryotic organisms including *aspergillus* (U.S. Pat. No. 6,080,559), cattle (U.S. Pat. No. 5,919,913), rice, corn, *Sacharomcyes* (U.S. Pat. No. 6,228,614) and *Pichia pastoris* (U.S. Pat. Nos. 6,455,687, 6,277,817, 6,066,469). Also described are expression systems for the expression of full-length human lactoferrins (e.g., U.S. Pat. No. 6,100,054). In all cases, part of the teaching is expression of the full-length cDNA and purification of the intact protein whose N-terminal, after processing of the leader peptide, is the amino acid glycine. Nuijens et al. (U.S. Pat. No. 6,333,311) separately describe variants of human lactoferrin but their focus is limited to deletion or substitution of arginine residues found in the N-terminal domain of lactoferrin.

Recently, bovine lactoferrin (bLF) was used as a prophylaxis for tumor formation and/or established tumors. The present invention is the first to use lactoferrin as cancer vaccine adjuvant for the prevention (prophylaxis) or treatment (therapeutic) of tumors.

BRIEF SUMMARY OF THE INVENTION

The present invention is directed to a method for preventing or treating cancer. The method of treatment involves administration of lactoferrin and a cancer immunotherapy, e.g., cancer vaccine. Thus, it is contemplated that lactoferrin can be used as an adjuvant for cancer immunotherapy.

The lactoferrin composition, which is dispersed in a pharmaceutically acceptable carrier, comprises lactoferrin or an N-terminal lactoferrin variant in which at least the N-terminal glycine residue is truncated or substituted. The lactoferrin is mammalian lactoferrin, more particularly, the lactoferrin is human or bovine. Yet further, the lactoferrin is recombinant lactoferrin. N-terminal lactoferrin variants include variants that at least lack the N-terminal glycine residue or contain a substitution at the N-terminal glycine residue. The substitution can comprise substituting a natural or artificial amino acid residue for the N-terminal glycine residue. For example, the substitution can comprise substituting a positive amino acid residue or a negative amino acid residue for the N-terminal glycine residue or substituting a neutral amino acid residue other than glycine for the N-terminal glycine residue. Other N-terminal lactoferrin variants include lactoferrin lacking one or more N-terminal residues or having one or more substitutions in the N-terminal. In specific embodiments, the N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition or any range in between.

The amount of the lactoferrin that is administered is about 1 mg to about 100 g per day, more preferably, the amount is about 10 mg to about 100 g per day. More particularly, the composition is a solution, capsule or a tablet having a lactoferrin concentration of about 0.01% to about 100%.

Another embodiment of the present invention comprises a method of treating cancer comprising the step of administering to a subject a cancer immunotherapy and an adjuvant, wherein the adjuvant is a lactoferrin composition that is administered in an amount sufficient to provide an improvement in the cancer in the subject. Still further, the method can further comprise additionally administering chemotherapy, immunotherapy, surgery, biotherapy, radiotherapy or a combination thereof to the subject.

It is envisioned that the lactoferrin composition can be administered orally, parenterally or topically. Parenterally includes, but is not limited subcutaneously, intramuscularly, intraperitoneally, intravenously, intraarterially, intramyocardially, transendocardially, transepicardially, or intrathecally. For oral administration, an antacid in combination with the lactoferrin composition can be administered. The lactoferrin composition can be formulated in a delayed release formulation. Still further, the lactoferrin composition can be formulated wherein release occurs in the small intestine or in the large intestine.

In specific embodiments, the cancer comprises a neoplasm. The neoplasm is selected from the group consisting of melanoma, non-small cell lung, small-cell lung, lung hepatocarcinoma, retinoblastoma, astrocytoma, gliobastoma, leukemia, neuroblastoma, squamous cell, head, neck, gum, tongue, breast, pancreatic, prostate, renal, bone, testicular, ovarian, mesothelioma, sarcoma, cervical, gastrointestinal, lymphoma, brain, colon, and bladder. More particularly, the neoplasm is a hematopoietic neoplasm. Exemplary hematopoietic neoplasms include, but are not limited to myelogenous leukemia, acute lymphoblastic leukemia, myelodysplastic syndrome, chronic myelomonocytic leukemia, juvenile myelomonocyte leukemia, multiple myeloma, and chronic lymphocytic leukemia.

In certain embodiments, the immunotherapy comprises antigen presenting cells. More specifically, the lactoferrin composition is administered ex vivo to the antigen presenting cells prior to administering the cells to the subject. The cells are allogeneic or syngeneic.

Still further, the immunotherapy comprises administration of a tumor antigen to the subject, or administration of a nucleic acid sequence expressing a cancer antigen to the subject. In specific embodiments, the nucleic acid sequence is contained in a vector.

Yet further, the immunotherapy comprises administration of a vector containing a nucleic acid sequence expressing an immunomodulatory cytokine to the subject.

Still further, the immunotherapy comprises administration of a protein or nucleic acid that promotes the recognition of a cancer antigen in the subject.

In certain embodiments, the lactoferrin composition is administered simultaneously and/or sequentially with the immunotherapy.

Another method of the present invention comprises a method of enhancing the immune system in a subject suffering from cancer or susceptible to cancer comprising the step of administering to the subject a cancer immunotherapy and an adjuvant, wherein the adjuvant is a lactoferrin composition. More specifically, the lactoferrin is administered orally.

In certain embodiments, lactoferrin stimulates the production of interleukin-18, GM-CSF, or MIP-3alpha. Yet further, interleukin-18, GM-CSF or MIP-3alpha stimulate the production, maturation, migration or activity of immune cells (e.g., T lymphocytes, natural killer cells, dendritic cells, antigen presenting cells or progenitor cell). More specifically, T lymphocytes are selected from the group consisting of CD4+, CD8+ and CD3+ cells.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
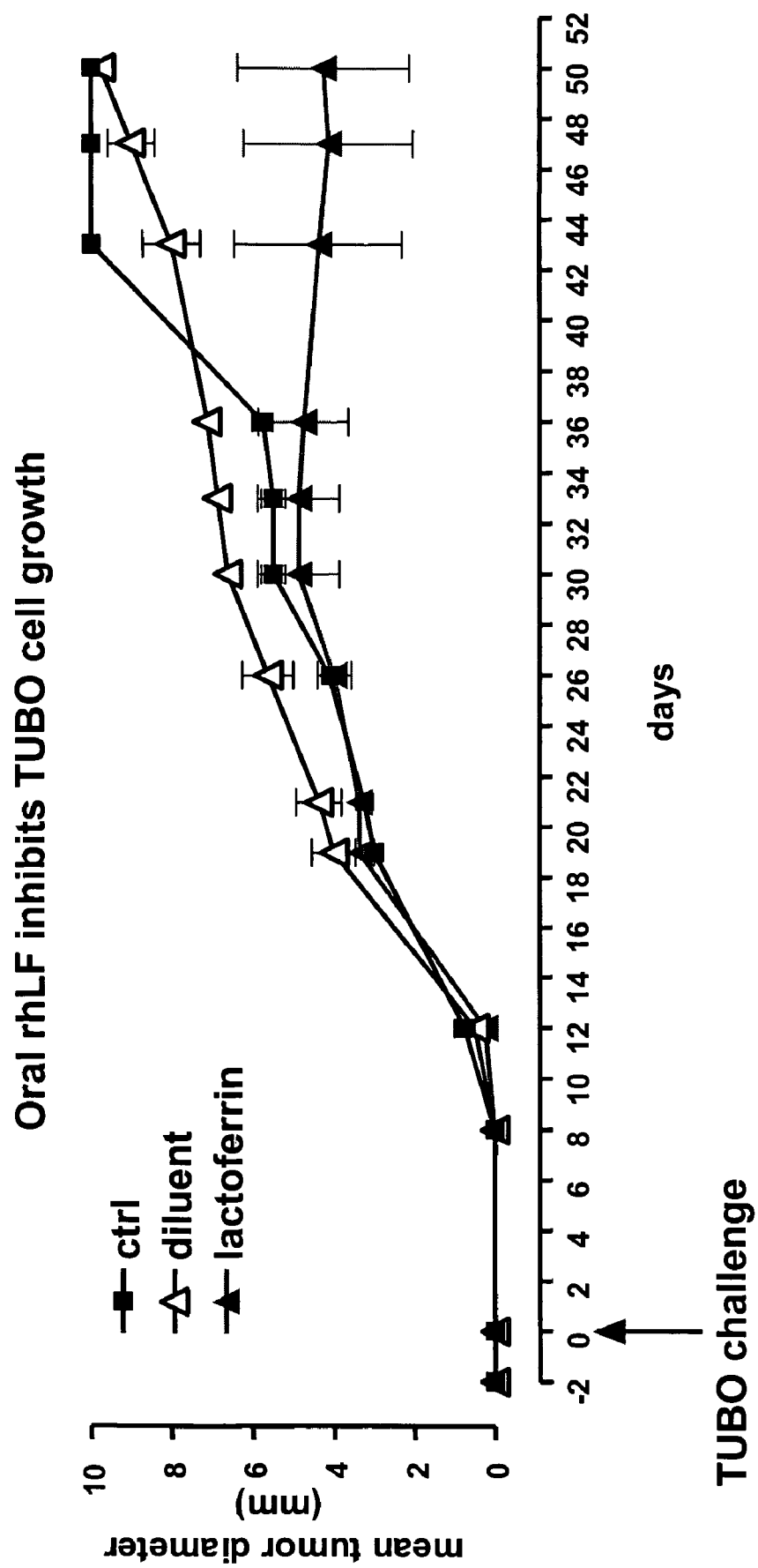
FIG. 1 shows carcinoma cell tumor growth with and without oral administration of lactoferrin.

It is readily apparent to one skilled in the art that various embodiments and modifications can be made to the invention disclosed in this Application without departing from the scope and spirit of the invention.

I. Definitions

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

The term "adjuvant" as used herein refers to substance added to drug product formulation that affects the action of the active ingredient by enhancing or potentiating its activity. An adjuvant also includes a treatment and/or therapy that is added or combined with a traditional treatment and/or therapy to enhance or potentiate or extend the effect of the traditional treatment and/or therapy.

The term "allogeneic" as used herein, refers to cell types or tissues that are antigenically distinct. Thus, cells or tissue transferred from the same species can be antigenically distinct.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates. Therefore, a skilled artisan realizes that any macromolecule, including virtually all proteins or peptides, can serve as antigens. Furthermore, antigens can be derived from recombinant or genomic DNA. A skilled artisan realizes that any DNA, which contains nucleotide sequences or partial nucleotide sequences of a pathogenic genome or a gene or a fragment of a gene for a protein that elicits an immune response results in synthesis of an antigen.

The term "antigen presenting cell" as used herein is any cell that enhances the immune response (i.e., from the T-cell or –B-cell arms of the immune system) against an antigen or antigenic composition.

The term "dendritic cell" or "DC" as used herein is defined as an example of an antigen presenting cell derived from bone marrow. Dendritic cells have a branched or dendritic morphology and are the most potent stimulations of T-cell response.

As used herein, the term "ex vivo" refers to "outside" the body. One of skill in the art is aware that ex vivo and in vitro can be used interchangeably.

The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intratumoral, intraocular, or intraarticular administration.

The term "oral administration" as used herein includes oral, buccal, enteral or intragastric administration.

The term "topical administration" as used herein includes application to a dermal, epidermal, subcutaneous or mucosal surface.

The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The term "lactoferrin composition" as used herein refers to a composition having lactoferrin, a portion or part of lactoferrin, an N-terminal lactoferrin variant, or a combination thereof.

The term "lactoferrin" or "LF" as used herein refers to native or recombinant lactoferrin. Native lactoferrin can be obtained by purification from mammalian milk or colostrum or from other natural sources. Recombinant lactoferrin (rLF) can be made by recombinant expression or direct production in genetically altered animals, plants, fungi, bacteria, or other prokaryotic or eukaryotic species, or through chemical synthesis.

The term "human lactoferrin" or "hLF" as used herein refers to native or recombinant human lactoferrin. Native human lactoferrin can be obtained by purification from human milk or colostrum or from other natural sources. Recombinant human lactoferrin (rhLF) can be made by recombinant expression or direct production in genetically altered animals, plants, fungi, bacteria, or other prokaryotic or eukaryotic species, or through chemical synthesis.

The term "bovine lactoferrin" or "bLF" as used herein refers to native or recombinant bovine lactoferrin. Native bovine lactoferrin can be obtained by purification from bovine milk. Recombinant bovine lactoferrin (rbLF) can be made by recombinant expression or direct production in genetically altered animals, plants, fungi, bacteria, or other prokaryotic or eukaryotic species, or through chemical synthesis.

The term "N-terminal lactoferrin variant" as used herein refers to lactoferrin wherein at least the N-terminal glycine has been truncated and/or substituted. N-terminal lactoferrin variants also include, but are not limited to deletion and/or substitution of one or more N-terminal amino acid residues, for example 1, 2, 3, 4, 5, 6, 7, 8, 9, 10, 11, 12, 13, 14, 15, or 16 N-terminal amino acid residues, etc. Thus, N-terminal lactoferrin variants comprise at least deletions or truncations and/or substitutions of 1 to 16 N-terminal amino acid residues. The deletion and/or substitution of at least the N-terminal glycine of lactoferrin mediates the same biological effects as full-length lactoferrin and/or may enhance lactoferrin's biological activity, for example by stimulating the production of various cytokines (e.g., IL-18, MIP-3α, GM-CSF or IFN-γ) by inhibiting various cytokines, (e.g., IL-2, IL-4, IL-5, IL-10, or TNF-α), and by improving other parameters which promotes or enhances the well-being of the subject with respect to the medical treatment of his/her cancer. A list of non-exhaustive examples of this includes extension of the subject's life by any period of time; decrease or delay in the neoplastic development of the disease; decrease in hyperproliferation; reduction in tumor growth; delay of metastases; reduction in the proliferation rate of a cancer cell, tumor cell, or any other hyperproliferative cell; induction of apoptosis in any treated cell or in any cell affected by a treated cell; and a decrease in pain to the subject that can be attributed to the subject's condition.

The term "subject" as used herein, is taken to mean any mammalian subject to which a human or bovine lactoferrin composition is orally, topical and/or parenterally administered according to the methods described herein. In a specific embodiment, the methods of the present invention are employed to treat a human subject. Another embodiment includes treating a human subject suffering from cancer.

As used herein, the term "syngeneic" refers to cells, tissues or animals that have genotypes. For example, identical twins or animals of the same inbred strain. Syngeneic and isogeneic can be used interchangeable.

The term "T-cell" as used herein is defined as a thymus-derived cell that participates in a variety of cell-mediated immune reactions.

The term "therapeutically effective amount" as used herein refers to an amount that results in an improvement or remediation of the symptoms of the disease or condition.

The term "treating" and "treatment" as used herein refers to administering to a subject a therapeutically effective amount of a lactoferrin composition so that the subject has an improvement in the disease. The improvement is any improvement or remediation of the symptoms. The improvement is an observable or measurable improvement. Thus, one of skill in the art realizes that a treatment may improve the disease condition, but may not be a complete cure for the disease.

The term "vaccine" as used herein is defined as material used to provoke an immune response (e.g., the production of antibodies) on administration of the materials and thus conferring immunity. Thus, a vaccine is an antigenic and/or immunogenic composition.

II. Lactoferrin

The lactoferrin used according to the present invention can be obtained through isolation and purification from natural sources, for example, but not limited to mammalian milk. The lactoferrin is preferably mammalian lactoferrin, such as bovine or human lactoferrin. In preferred embodiments, the lactoferrin is produced recombinantly using genetic engineering techniques well known and used in the art, such as recombinant expression or direct production in genetically altered animals, plants or eukaryotes, or chemical synthesis.

See, for example, U.S. Pat. Nos. 5,571,896; 5,571,697 and 5,571,691, which are herein incorporated by reference.

In certain aspects, the present invention provides lactoferrin variants having enhanced biological activities over natural LF and or rLF, e.g., the ability to stimulate and/or inhibit cytokines or chemokines. In particular, the invention provides variants of lactoferrin from which at least the N-terminal glycine residue has been substituted and/or truncated. The N-terminal lactoferrin variants may occur naturally or may be modified by the substitution or deletion of one or more amino acids.

The deletional variants can be produced by proteolysis of lactoferrin and/or expression of a polynucleotide encoding a truncated lactoferrin as described in U.S. Pat. No. 6,333,311, which is incorporated herein by reference.

Substitutional variants or replacement variants typically contain the exchange of one amino acid for another at one or more sites within the protein. Substitutions can be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, e.g., still obtain a biological functionally equivalent protein. In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5 ±1); alanine (−0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4).

Still further, it is understood that an amino acid can be substituted for another having a similar hydrophilicity value and still obtains a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

Thus, in the present invention, substitutional variants or replacement can be produced using standard mutagenesis techniques, for example, site-directed mutagenesis as disclosed in U.S. Pat. Nos. 5,220,007; 5,284,760; 5,354,670; 5,366,878; 5,389,514; 5,635,377; 5,789,166, and 6,333,311, which are incorporated herein by reference. It is envisioned that at least the N-terminal glycine amino acid residue can be replaced or substituted with any of the twenty natural occurring amino acids, for example a positively charged amino acid (arginine, lysine, or histidine), a neutral amino acid (alanine, asparagine, cysteine, glutamine, glycine, isoleucine, leucine, methionine, phenylaline, proline, serine, threonine, tryptophan, tyrosine, valine) and/or a negatively charged amino acid (aspartic acid or glutamic acid). Still further, it is contemplated that any amino acid residue within the range of N1 to N16 can be replaced or substituted. It is envisioned that at least up to 16 of the N-terminal amino acids residues can be replaced or substituted as long as the protein retains it biological and/or functional activity, which is stimulating the production of various cytokines, (e.g., IL-18, MIP-3α, GM-CSF or IFN-γ) by inhibiting various cytokines, (e.g., IL-2, IL-4, IL-5, IL-10, and TNF-α) and/or by improving the parameters related to which promotes or enhances the well-being of the subject with respect to the medical treatment of his/her cancer. A list of non-exhaustive examples of this includes extension of the subject's life by any period of time; decrease or delay in the neoplastic development of the disease; decrease in hyperproliferation; reduction in tumor growth; delay of metastases; reduction in the proliferation rate of a cancer cell, tumor cell, or any other hyperproliferative cell; induction of apoptosis in any treated cell or in any cell affected by a treated cell; and a decrease in pain to the subject that can be attributed to the subject's condition. Thus, the N-terminal lactoferrin variants of the present invention are considered functional equivalents of lactoferrin.

In terms of functional equivalents, it is well understood by the skilled artisan that, inherent in the definition of a "biologically functional equivalent" protein is the concept that there is a limit to the number of changes that may be made within a defined portion of the molecule while retaining a molecule with an acceptable level of equivalent biological activity and/or enhancing the biological activity of the lactoferrin molecule. Biologically functional equivalents are thus defined herein as those proteins in which selected amino acids (or codons) may be substituted. Functional activity is defined as the ability of lactoferrin to stimulate or inhibit various cytokines or chemokines and/or by improving the parameters which promotes or enhances which promotes or enhances the well-being of the subject with respect to the medical treatment of his/her cancer. For example, extension of the subject's life by any period of time; decrease or delay in the neoplastic development of the disease; decrease in hyperproliferation; reduction in tumor growth; delay of metastases; reduction in the proliferation rate of a cancer cell, tumor cell, or any other hyperproliferative cell; induction of apoptosis in any treated cell or in any cell affected by a treated cell; and a decrease in pain to the subject that can be attributed to the subject's condition.

Still further, the N-terminal amino acid residues can be substituted with a modified and/or unusual amino acids. A table of exemplary, but not limiting, modified and/or unusual amino acids is provided herein below.

TABLE 1

Modified and/or Unusual Amino Acids

| Abbr. | Amino Acid |
|---|---|
| Aad | 2-Aminoadipic acid |
| BAad | 3-Aminoadipic acid |
| BAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

The presence and the relative proportion of an N-terminal lactoferrin variants (deletions and/or substitutions) in a preparation of lactoferrin (lactoferrin composition) may be done by determination of the N-terminal amino acid sequence by the process of Edman degradation using standard methods. A relative proportion of N-terminal lactoferrin variant comprises at least 1% of the lactoferrin composition, at least 5% of the lactoferrin composition, at least 10% of the lactoferrin composition, at least 25% of the lactoferrin composition, at least 50% of the lactoferrin composition or any range in between.

In this method, the protein is reacted with phenylisothiocyanate (PITC), which reacts with the amino acid residue at the amino terminus under basic conditions to form a phenylthiocarbamyl derivative (PTC-protein). Trifluoroacetic acid then cleaves off the first amino acid as its anilinothialinone derivative (ATZ-amino acid) and leaves the new amino terminus for the next degradation cycle.

The percentage of N-terminal lactoferrin variant may also be done more precisely by using a Dansylation reaction. Briefly, protein is dansylated using Dansyl chloride reacted with the protein in alkaline conditions (pH 10). Following the Dansylation, the reaction mixtures are dried to pellets, then completely hydrolyzed in 6N HCl. The proportion of N-terminal amino acids are identified by RP HPLC using an in-line fluorometer in comparison with standards made up of known dansylated amino acids.

III. Pharmaceutical Compositions

The present invention is drawn to a composition comprising lactoferrin that is dispersed in a pharmaceutical carrier. The lactoferrin that is contained in the composition of the present invention comprises lactoferrin or an N-terminal lactoferrin variant in which at least the N-1 terminal glycine residue is truncated or substituted. N-terminal lactoferrin variants include variants that at least lack the N-terminal glycine residue or contain a substitution at the N-terminal glycine residue. The substitution can comprise substituting a natural or artificial amino acid residue for the N-terminal glycine residue. For example, the substitution can comprise substituting a positive amino acid residue or a negative amino acid residue for the N-terminal glycine residue or substituting a neutral amino acid residue other than glycine for the N-terminal glycine residue. Other N-terminal lactoferrin variants include lactoferrin lacking one or more N-terminal residues or having one or more substitutions in the N-terminal. The N-terminal lactoferrin variant comprises at least 1% of the composition, at least 5% of the composition, at least 10% of the composition, at least 25% of the composition, at least 50% of the composition or any range in between.

Further in accordance with the present invention, the composition of the present invention suitable for administration is provided in a pharmaceutically acceptable carrier with or without an inert diluent. The carrier should be assimilable and includes liquid, semi-solid, e.g., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof.

In accordance with the present invention, the composition is combined with the carrier in any convenient and practical manner, e.g., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, e.g., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc., proteolytic enzyme inhibitors, and the like. Yet further, it is envisioned that divalent metal chelators, for example EDTA, can also be used to stabilize the composition of the present invention. More preferably, for an orally administered composition, the stabilizer can also include antagonists to the secretion of stomach acids.

Administration of the lactoferrin compositions according to the present invention will be via any common route, orally, parenterally, or topically. Exemplary routes include, but are not limited to oral, nasal, buccal, rectal, vaginal, parenteral, intramuscular, intraperitoneal, intravenous, intraarterial, intratumoral, topical or dermal. Such compositions would normally be administered as pharmaceutically acceptable compositions as described herein.

The composition for oral administration which is combined with a semi-solid or solid carrier can be further formulated into hard or soft shell gelatin capsules, tablets, or pills.

More preferably, gelatin capsules, tablets, or pills are enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the lactoferrin composition to be released and absorbed by specialized cells, e.g., epithelial enterocytes and Peyer's patch M cells.

In another embodiment, a powdered composition is combined with a liquid carrier such as, e.g., water or a saline solution, with or without a stabilizing agent.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Sterile injectable solutions are prepared by incorporating the lactoferrin in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Further, a composition for topical administration which is combined with a semi-solid carrier can be further formulated into a gel ointment. A preferred carrier for the formation of a gel ointment is a gel polymer. Preferred polymers that are used to manufacture a gel composition of the present invention include, but are not limited to carbopol, carboxymethylcellulose, and pluronic polymers. Specifically, a powdered lactoferrin composition is combined with an aqueous gel containing an polymerization agent such as Carbopol 980 at strengths between 0.01% and 5% wt/volume for application to the skin for treatment of cancer on or beneath the skin.

The amount of lactoferrin in the present invention may vary from about 1 mg to about 100 g of lactoferrin, more preferably 1 mg to 100 g per day. In preferred embodiments, the composition of the present invention comprises a lactoferrin concentration of about 0.01% to about 100%. The lactoferrin composition may comprise lactoferrin or an N-terminal lactoferrin variant in which at least the N-1 terminal glycine residue is truncated and/or substituted.

Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Office of Biologics standards.

IV. Treatment of Cancer

In accordance with the present invention, a lactoferrin composition provided in any of the above-described pharmaceutical carriers is administered in combination with a cancer immunotherapy or vaccine to a subject suspected of or having cancer. Thus, one of skill in the art realizes that lactoferrin is acting an adjuvant. The process involves administering a lactoferrin composition of the present invention and the immunotherapy agent(s) or multiple factor(s) at the same time. This may be achieved by administering a single composition or pharmacological formulation that includes both agents (lactoferrin and the cancer vaccine), or by administering two distinct compositions or formulations, at the same time, or at times close enough so as to result in an overlap of this effect, wherein one composition includes lactoferrin composition and the other includes the cancer vaccine. It is also contemplated that the lactoferrin composition and the cancer vaccine can be administered sequentially.

Cancer, includes but is not limited to neoplasms. A neoplasm is an abnormal tissue growth, generally forming a distinct mass that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias, lymphomas and myelomas. A tumor is the neoplastic growth of the disease cancer. As used herein, a "neoplasm", also referred to as a "tumor", is intended to encompass hematopoietic neoplasms as well as solid neoplasms. Examples of neoplasms include, but are not limited to melanoma, non-small cell lung, small-cell lung, lung, hepatocarcinoma, retinoblastoma, astrocytoma, gliobastoma, gum, tongue, leukemia, neuroblastoma, head, neck, breast, pancreatic, prostate, renal, bone, testicular, ovarian, mesothelioma, sarcoma, cervical, gastrointestinal, lymphoma, brain, colon, bladder, myeloma, or other malignant or benign neoplasms.

More particularly, the neoplasm is a hematopoietic neoplasm which is selected from the group consisting of acute myelogenous leukemia, acute lymphoblastic leukemia, myelodysplastic syndrome, chronic myelomonocytic leukemia, juvenile myelomonocyte leukemia, multiple myeloma, and chronic lymphocytic leukemia.

A. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Improvements in the identification of tumor-associated antigens have spurred the generation of new vaccine strategies (Sabel. et al., 2002). These strategies can be divided into two categories: antigen-specific vaccines, in which the tumor antigens have been identified and can be isolated to develop a molecularly defined vaccine, and cellular or non-antigen specific, in which the tumor-specific antigens are unknown but presumed to exist within the material used to generate the vaccine (Borrello et al., 2002). Tumor-specific antigens can be divided into four categories: unique tumor-specific antigens that are the products of mutation; viral antigens in virus-associated cancers; tissue-specific differentiation antigens; and tumor-selective antigens (D. Pardoll, 2002)

Active immunization against cancer can be achieved delivering tumor-specific peptide vaccines to patients along with an immune adjuvant meant to induce inflammation and stimulate immunity (Machiels et al., 2002). An alternative approach is the use of cellular vaccines. Autologous cellular vaccines present biologically relevant antigens to the immune system, but this is limited to individuals with sufficient tumor to prepare a vaccine (Chang et al., 2003) Allogeneic cellular vaccines are based on the fact that tumor-associated antigens are shared among a large number of patients, so a vaccine prepared from a cultured cell line could stimulate an antitumor immune response in many patients (Vaishampayan et al., 2002). Several additional approaches to vaccine therapies include among others ganglioside vaccines (Knutson, 2002) viral oncolysates (Horvath et al., 1999), anti-idiotype antibodies (Alfonso et al., 2002), cytokine gene-modified tumor cell vaccines (Forni et al., 2000), dendritic cell vaccines (Curiel et al., 2002), and DNA vaccines (Bronte, 2001).

Such vaccines include peptide vaccines or dendritic cell vaccines. Peptide vaccines may include any tumor-specific antigen that is recognized by cytolytic T lymphocytes. Yet further, one skilled in the art realizes that dendritic cell vaccination comprises dendritic cells that are pulsed with a peptide or antigen and the pulsed dendritic cells are administered to the patient.

B. Treatments

The present invention contemplates the treatment of cancer. It is envisioned that the present invention is directed at the use of the cancer immunotherapy in combination with a lactoferrin composition to treat subjects with cancer such that these subjects are conferred a therapeutic benefit as a result of the treatment. Thus, a therapeutic benefit refers to a result that promotes or enhances the well-being of the subject with respect to the medical treatment of his/her cancer. A list of non-exhaustive examples of this includes extension of the subject's life by any period of time; decrease or delay in the neoplastic development of the disease; decrease in hyperproliferation; reduction in tumor growth; delay of metastases; reduction in the proliferation rate of a cancer cell, tumor cell, or any other hyperproliferative cell; induction of apoptosis in any treated cell or in any cell affected by a treated cell; and a decrease in pain to the subject that can be attributed to the subject's condition.

Treatment regimens may vary as well, and often depend on cancer vaccine used, tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In a preferred embodiment of the present invention, lactoferrin is administered in an effective amount to potentiate the effect of the immunotherapy which is to decrease, reduce, inhibit or abrogate the growth of a tumor. The amount of the lactoferrin composition may vary from about 1 mg to about 100 g of lactoferrin.

In specific embodiments, the lactoferrin composition is given in a single dose or multiple doses. The single dose may be administered daily, or multiple times a day, or multiple times a week, or monthly or multiple times a month. In a further embodiment, the lactoferrin composition is given in a series of doses. The series of doses may be administered daily, or multiple times a day, weekly, or multiple times a week, or monthly, or multiple times a month.

Specifically, the present invention intends to provide, to a cell, an antigen-specific vaccines and/or DNA vaccines in combination with an effective amount of lactoferrin to potentiate the effect of the antigen-specific vaccine. The discussion of antigen-specific vaccines is incorporated into this section by reference. Thus, one of skill in the art is well aware of how to apply gene delivery and/or DNA delivery to in vivo and ex vivo situations.

Another therapy that is contemplated is the administration of transduced antigen presenting cells and/or dendritic cell vaccines. The antigen presenting cells and/or dendritic cells are transduced in vitro or ex vivo with an antigen-specific DNA. The transduced antigen presenting cells and/or dendritic cells are then administered in combination with a lactoferrin composition.

Still further, the present invention includes a method of enhancing the immune response in an subject suffering from or susceptible to cancer comprising the steps of administering an antigen presenting cell that contains the DNA vaccine in combination with a lactoferrin composition. The antigen presenting cells may be obtained from the blood of the subject or bone marrow of the subject. In certain preferred embodiments, the antigen presenting cells are isolated from the bone marrow. In a preferred embodiment, the antigen presenting cells are administered to the same or different subject (e.g., same or different donors). In a preferred embodiment, the subject has or is suspected of having a cancer, A further embodiment of the present invention is a method of treating a cancer comprising the step of supplementing a mucosal or systemic immune system by increasing the amount of a lactoferrin composition in the gastrointestinal tract and/or in the systemic circulation.

Still yet, a further embodiment is a method of enhancing a mucosal immune response in the gastrointestinal tract in a subject comprising the step of administering orally to said subject a human lactoferrin. It is envisioned that human lactoferrin stimulates interleukin-18 in the gastrointestinal tract, which enhances immune cells. For example, interleukin-18 enhances T lymphocytes or natural killer cells. In specific embodiments, interleukin-18 (IL-18) enhances CD4+, CD8+ and CD3+ cells. It is known by those of skill in the art that IL-18 is a Th1 cytokine that acts in synergy with interleukin-12 and interleukin-2 in the stimulation of lymphocyte IFN-gamma production. Other cytokines may also be enhanced for example, but not limited to IL-1b or, IL-12 or IFN-gamma. It is also envisioned that human lactoferrin stimulates interleukin-18 following oral administration, which inhibits angiogenesis and thereby has activity against tumor cells which are dependent on neovascularization.

V. Combination Treatments

In order to increase the effectiveness of the cancer vaccine/adjuvant (lactoferrin composition of the present invention), it may be desirable to combine the cancer vaccine/adjuvant composition of the present invention with other agents effective in the treatment of cancer, such as anti-cancer agents, or with surgery. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve administering the cancer vaccine/adjuvant composition of the present invention and the agent(s) or multiple factor(s) at the same time. This may be achieved by administering a single composition or pharmacological formulation that includes both agents, or by administering two distinct compositions or formulations, at the same time, or at times close enough so as to result in an overlap of this effect, wherein one composition includes the cancer vaccine/adjuvant composition and the other includes the second agent(s).

Alternatively, the cancer vaccine/adjuvant composition of the present invention may precede or follow the other anti-cancer agent treatment by intervals ranging from minutes to weeks. In embodiments where the other anti-cancer agent and cancer vaccine/adjuvant composition are administered or applied separately to the cell, one would generally ensure that a significant period of time did not expire between the time of each delivery, such that the agent and lactoferrin composition would still be able to exert an advantageously combined effect on the cell. In such instances, it is contemplated that one may contact the cell with/administer both modalities within about 1-14 days of each other and, more preferably, within about 12-24 hours of each other. In some situations, it may be desirable to extend the time period for treatment significantly, however, where several days (2, 3, 4, 5, 6 or 7) to several weeks (2, 3, 4, 5, 6, 7 or 8) lapse between the respective administrations.

A. Chemotherapy

Cancer therapies also include a variety of chemical based treatments. Some examples of chemotherapeutic agents include without limitation antibiotic chemotherapeutics such as Doxorubicin, Daunorubicin, Adriamycin, Mitomycin (also known as mutamycin and/or mitomycin-C), Actinomycin D (Dactinomycin), Bleomycin, Plicomycin, plant alkaloids such as Taxol, Vincristine, Vinblastine, miscellaneous agents such as Cisplatin (CDDP), etoposide (VP16), Tumor Necrosis Factor, and alkylating agents such as, Carmustine, Melphalan (also known as alkeran, L-phenylalanine mustard, phenylalanine mustard, L-PAM, or L-sarcolysin, (a phenylalanine derivative of nitrogen mustard), Cyclophosphamide, Chlorambucil, Busulfan (also known as myleran), and Lomustine.

Some examples of other agents include, but are not limited to, Carboplatin, Procarbazine, Mechlorethamine, Irinotecan, Topotecan, Ifosfamide, Nitrosurea, Etoposide (VP16), Tamoxifen, Raloxifene, Toremifene, Idoxifene, Droloxifene, TAT-59, Zindoxifene, Trioxifene, ICI 182,780, EM-800, Estrogen Receptor Binding Agents, Gemcitabinen, Navelbine, Farnesyl-protein transferase inhibitors, Transplatinum, 5-Fluorouracil, hydrogen peroxide, and Methotrexate, Temazolomide (an aqueous form of DTIC), Mylotarg, Dolastatin-10, Bryostatin, or any analog or derivative variant of the foregoing.

B. Radiotherapeutic Agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage to DNA, the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

C. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

D. Other Biotherapy Agents

It is contemplated that other biological agents may be used in combination with the present invention to improve the therapeutic efficacy of treatment. These additional agents include, without limitation, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents, as well as biotherapy such as for example, hyperthermia.

Hyperthermia is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention. The use of hormones may be employed in the treatment of certain cancers such as breast, prostate, ovarian, or cervical cancer to lower the level or block the effects of certain hormones such as testosterone or estrogen and this often reduces the risk of metastases.

Adjuvant therapy may also be used in conjunction with the present invention. The use of adjuvants or immunomodulatory agents include, but are not limited to tumor necrosis factor; interferon alpha, beta, and gamma; IL-2 and other cytokines; F42K and other cytokine analogs; or MIP-1, MIP-1beta, MCP-1, RANTES, and other chemokines.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Oral LF Inhibits the Growth of Her-2/neu+Transplantable Carcinoma (TUBO)

Briefly, BALB/C mice were challenged subcutaneously (s.c.) in the middle of the left flank with 0.2 ml of a single-cell suspension containing $1 \times 10^5$ TUBO cells. Oral rhLF or placebo was administered (1000 mg/kg/once a day) two days before TUBO injection and for 3 weeks (five days/week with a total of 15 treatments). Tumors were measured twice a week for the duration of the experiment. FIG. 1 shows that mice (4/group) treated with oral rhLF displayed a significant tumor inhibition (p<0.05 vs. placebo or ctrl) whereas no activity was observed in mice treated with placebo or left untreated.

Results from this study show that rhLF administered orally significantly (p<0.05) inhibits tumor growth of a transplantable carcinoma over-expressing the Her-2/neu (r-p185) oncogene. Based upon these results, it is further contemplated that oral lactoferrin affects the tumor by enhancing immune cell activity against tumor-specific antigen (Her-2/neu).

Example 2

Evaluation of rhLF as Adjuvant of p185 DNA Vaccine in the Prevention of TUBO

The adjuvant effect of oral LF in combination with DNA vaccination is evaluated. It is determined if oral LF in combination with a DNA vaccine will elicit complete protection against a lethal challenge of syngeneic carcinoma cells expressing p185 (TUBO) in BALB/C mice. The DNA vaccine consists of a plasmid encoding for the transmembrane (TM) and extracellular domain (ECD) of the rat p185 (r-p185). Overexpression of p185 is frequent in human cancers and correlates with particular aggressiveness (Gullick et al., 1991).

The p185 vector is constructed as follows. The pCMV vector is derived from the pcDNA3 plasmid (Invitrogen, San Diego, Calif.) by deleting the SV40 promoter, neomycin resistance gene, and SV40 poly(A). The sequence for the ECD and that for the ECD and TM domain of mutated r-p185 are generated from the PCR product using the primers SEQ.ID.NO:1 3'-CGCAAGCTTCATCATGGAGCTGGC-5' and SEQ.ID.NO:2 3'-CGGAATTCGGGCTGGCTCTCT-GCTC-5' and the primers SEQ.ID.NO:3 3'-CGCAAGCT-TCATGGAGCTGGC-5' and SEQ.ID.NO:4 3'-ATGAAT-TCTTTCCGCATCGTGTACTTCTTCCGG-5', respectively, as described by Amici et al. (Cancer Immunol. Immunother., 1998). PCR products of the expected size are isolated by agarose gel electrophoresis, digested with HindIII and EcoRI, and cloned into the multiple cloning site of the pCMV plasmid to obtain the two plasmids used in this work (ECD and ECD-TM plasmids). The pCMVb (Clontech Laboratories, Palo Alto, Calif.) coding for β-galactosidase is used as a control plasmid (β-gal plasmid). *Escherichia coli* strain DH5a is transformed with ECD, ECD-TM, and β-gal plasmids and then grown in Luria-Bertani medium (Sigma, St. Louis, Mo). Large-scale preparation of the plasmids is conducted by alkaline lysis using Endofree Qiagen Plasmid-Giga kits (Qiagen, Chatsworth, Calif.). DNA is then precipitated, suspended in sterile saline at the concentration of 1 mg/ml, and stored in aliquots at −20° C. for subsequent use in immunization protocols.

BALB/C mice are immunized twice intramuscularly (i.m.) with ECD-TM plasmid seven days before and after TUBO challenge with 14 days of interval between immunizations. The plasmids (100 mg/injection) are injected into the quadriceps muscle through a 28-gauge needle syringe. Oral lactoferrin (1000 mg/Kg) is administered daily starting seven days before TUBO challenge for three weeks of five treatments per week for a total 15 treatments. Control animals are treated with oral placebo and DNA vaccination; no rhLF is administered to the control animals.

The efficacy of treatment is evaluated by measuring the solid tumor size during and at the end of the experiment. Tumor masses are measured bi-weekly with calipers in the two perpendicular diameters. Progressively growing masses of >3 mm in mean diameter are regarded as tumors. Growth is monitored until tumors exceed an average diameter of 10 mm, at which time mice are sacrificed for humane reasons.

The immune response is measured by the morphological analysis of tumor infiltration depicting $CD4^+$ and $CD8^+$ T lymphocytes, polymorhonuclear cells (PMN), macrophages, NK and dendritic cells. Expression of endothelial cell adhesion molecules is also analyzed in tumor vessels. Cytokine profiles obtained from tumors and immune cell infiltration provides further insight into the mechanism of action. Anti-r-p185 antibodies are also analyzed in the sera of ECD-TM vaccinated mice and treated with oral LF to detect an antibody response against TUBO. CTL activity against TUBO cells is also analyzed in spleen of mice treated with oral LF and ECD-TM immunized versus control groups.

Example 3

Evaluation of rhLF as Adjuvant of p185 DNA Vaccine in the Treatment of TUBO

In this study, the adjuvant effect of oral LF in combination with DNA vaccination to inhibit the growth of established carcinoma expressing p185 (TUBO) in BALB/C mice is evaluated.

The efficacy of treatment is evaluated by measuring the solid tumor size during and at the end of the experiment. Tumor masses are measured bi-weekly with calipers in the two perpendicular diameters. Progressively growing masses of >3 mm in mean diameter are regarded as tumors. Growth is monitored until tumors exceed an average diameter of 10 mm, at which time mice are sacrificed for humane reasons.

The immune response is measured by the morphological analysis of tumor infiltration depicting $CD4^+$ and $CD8^+$ T lymphocytes, polymorhonuclear cells (PMN), macrophages, NK and dendritic cells. Expression of endothelial cell adhesion molecules is also analyzed in tumor vessels. Cytokine profiles obtained from tumors and immune cell infiltration provides further insight into the mechanism of action. Anti-r-p185 antibodies are also analyzed in the sera of ECD-TM vaccinated mice and treated with oral LF to detect an antibody response against TUBO. CTL activity against TUBO cells is also analyzed in spleen of mice treated with oral LF and ECD-TM immunized versus control groups.

Example 4

Oral LF in the Inhibition of Spontaneous Carcinomas

LF is orally administered daily for a three week course of five days/week followed by one week off from week 5 to 20 (total of five courses). Control mice receive oral placebo following the same schedule; no LF is administered to control animals.

Starting at the age of five week, mammary glands of each mouse are inspected once a week, and masses are measured with calipers in the two perpendicular diameters. Tumor-free mice (%) as well as mean number of tumors per mouse are recorded. Mice displaying progressively masses in all 10 mammary glands and those that reach 33 week of age are killed and morphologically examined.

Histological examination of the mammary gland at progressive time points in a fashion blind to the treatment reveals the progression of the HER-2/neu oncogenesis in the treated mice. The incidence of atypical hyperplasia (week 10) and the number of carcinoma in situ (week 15) shows the anti-tumor activity induced by oral LF in combination with tumor cell vaccination. Tumor progression is associated with neovascularization and lack of infiltrating $CD8^+$, and to a lesser extent $CD4^+$, lymphocytes evident by histology analysis of animals. The level of vascularization and T cell infiltration in tumors treated with LF reveals the activity of oral LF.

To evaluate the role of $CD8^+$ T cells in response to oral LF, BALB-NeuT mice treated with oral LF (same schedule as above) are thymectomized at 4 week and receive 200 ug of anti-CD8 antibody intraperitoneally. Starting at the age of five week, mammary glands of each mouse are inspected once a week, and masses are measured with calipers in the two perpendicular diameters.

Example 5

Oral LF and DNA Vaccination in the Inhibition of Spontaneous Carcinomas

In this study, the ability of oral LF in combination with DNA vaccination to hamper the aggressive carcinogenesis that takes place in all mammary glands of BALB-NeuT mice is evaluated.

Figure 3:
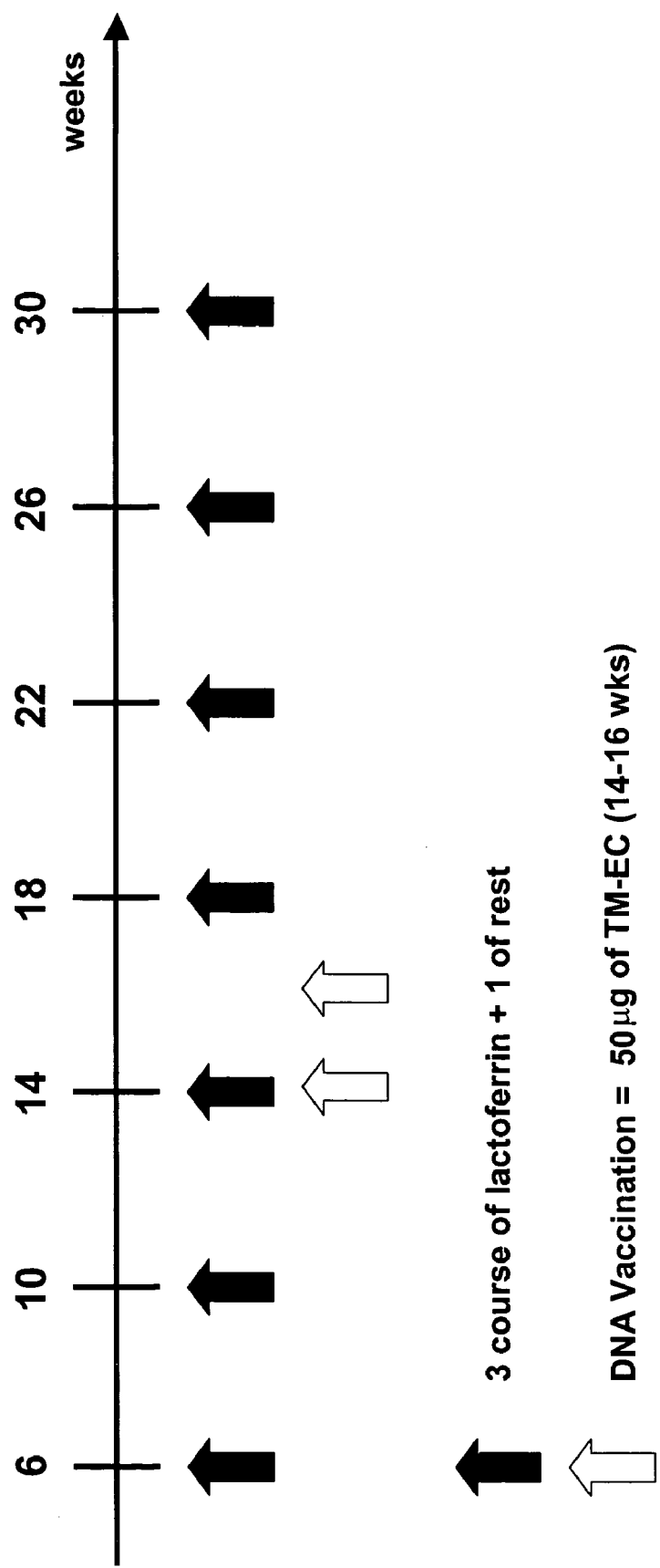
FIG. 3 shows and ECD-TM vaccination and oral LF schedule.

BALB-NeuT mice were immunized at the $14^{th}$ and $16^{th}$ week of age with the ECD-TM plasmid and treated with oral LF (1000 mg/Kg) daily for a three week course of five days/week followed by one week off from week 6 to 30 (total of seven courses) (FIG. 3). Control mice received only ECD-TM vaccination, oral FL, oral placebo (seven courses) or left untreated. The efficacy of individual and combination treatments was evaluated by weekly inspection of mice to follow tumor onset and growth. Tumor masses were measured with calipers in the two perpendicular diameters and tumor-free mice (%) as well as mean number of tumors per mouse was recorded. Mice displaying progressively masses in all 10 mammary glands were sacrificed for humane reasons.

Figure 4A:
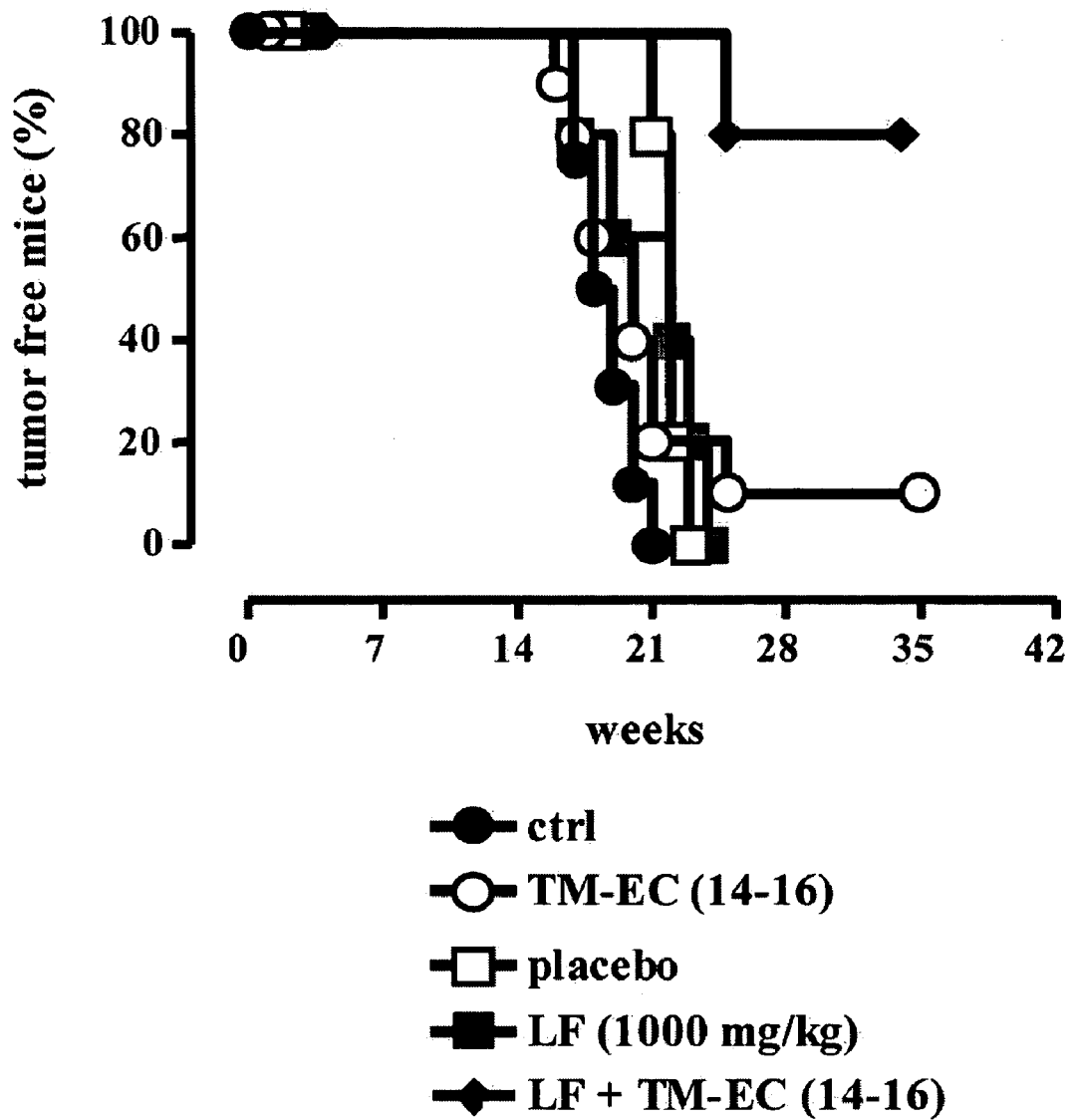
FIG. 4A and FIG. 4B show the effect of oral LF in combination with ECD-TM vaccination n carcinogenesis in BALB-neuT mice.
Figure 4B:
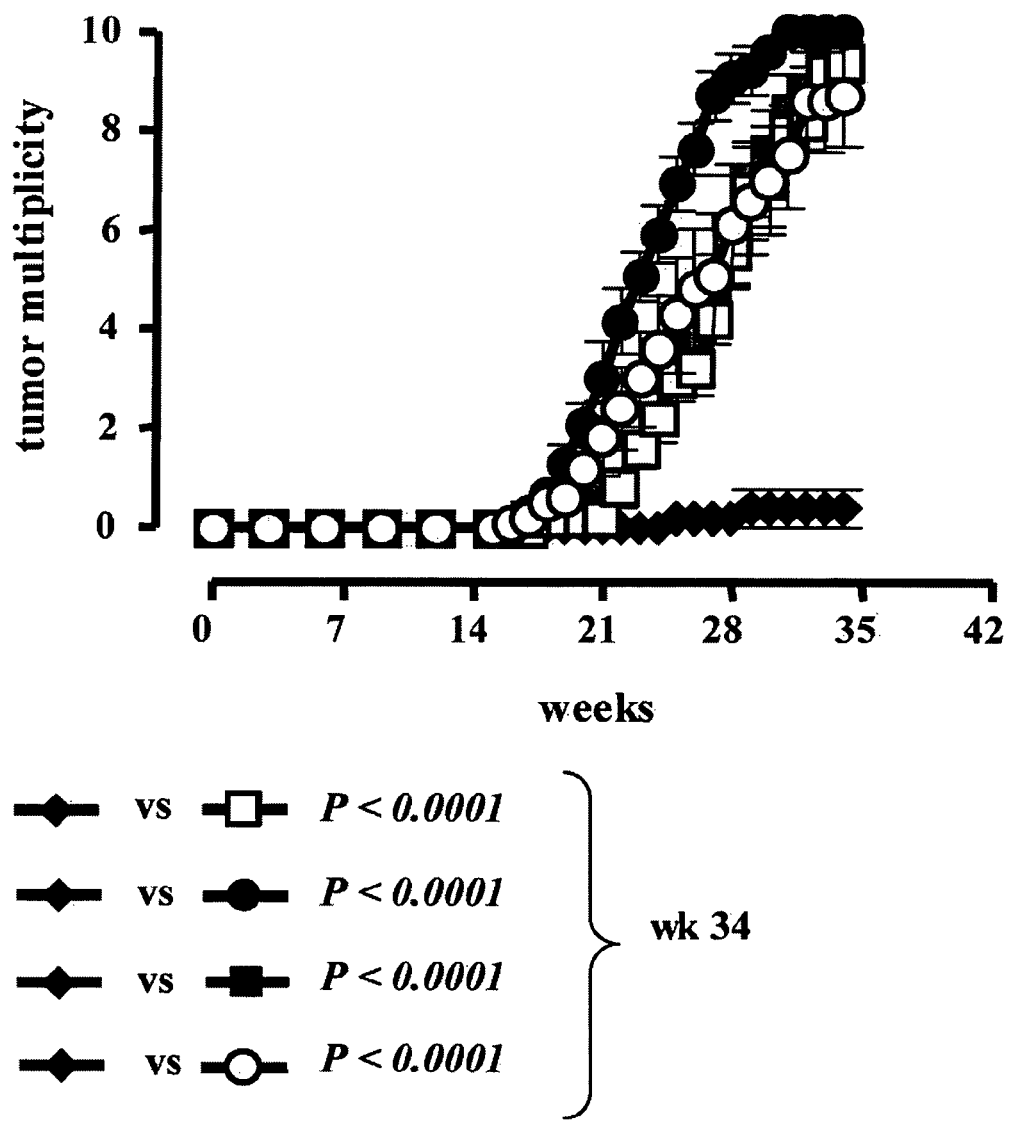

FIG. 4 shows that at week 34, when only 20% of mice vaccinated with ECD-TM did not have palpable mass in all 10 mammary glands, 80% of the mice treated with oral LF in combination with ECD-TM were tumor free (FIG. 4A). A significant reduction in tumor multiplicity was also evident (FIG. 4B).

Time of appearance of the first tumor (FIG. 4A) and mean number of palpable mammary carcinomas per mouse (FIG. 4B) in the group of 15 untreated (filled circle), 15 vaccinated (open circle), 5 placebo-treated (open square), 5 LF-treated (filled square) and 5 LF treated+vaccinated mice (filled diamond).

Histological examination of the mammary gland at progressive time points in a fashion blind to the treatment reveals the progression of the HER-2/neu oncogenesis in the treated mice. The incidence of atypical hyperplasia (week 10) and the number of carcinoma in situ (week 15) shows the anti-tumor activity induced by oral LF in combination with DNA vaccination. Tumor progression is associated with neovascularization and lack of infiltrating $CD8^+$, and to a lesser extent $CD4^+$, lymphocytes evident by histology analysis of animals. The level of vascularization and T cell infiltration in tumors treated with LF reveals the activity of oral LF.

To evaluate the role of $CD8^+$ T cells in response to oral LF, and DNA vaccination, BALB-NeuT mice immunized with ECD-TM plasmid and treated with oral LF (same schedule as above) are thymectomized at 4 week and receive 200 ug of anti-CD8 antibody intraperitoneally. Starting at the age of five week, mammary glands of each mouse are inspected once a week, and masses are measured with calipers in the two perpendicular diameters. Tumor-free mice (%) as well as mean number of tumors per mouse are recorded.

Example 6

Oral LF in Combination with Tumor Cell Vaccination in the Inhibition of Spontaneous Carcinoma The ability of oral LF in combination with allogeneic tumor vaccination to hamper mammary carcinogenesis in HER-2/neu transgenic mice is evaluated.

BALB-NeuT mice are vaccinated with allogeneic mammary carcinoma cells (Neu/H-$2^q$) expressing high surface levels of both p185neu and H-$2^q$ class I molecules (Nanni et al., 2001) and treated with oral LF. Beginning when mice are 6 week old, they receive Neu/H-2q cells twice-weekly in the first and second week followed by one week off. After one week of rest this course is repeated until week 33. Mice are also treated with oral LF (300 mg/Kg) daily for a three week course of five days/week followed by one week off from week 5 to 20 (total of five courses). Control mice receive oral placebo and allogeneic tumor cell vaccination schedule. The efficacy of individual and combination treatments is evaluated by weekly inspection of mice to follow tumor onset and growth. Tumor masses are measured with calipers in the two perpendicular diameters and tumor-free mice (%) as well as mean number of tumors per mouse is recorded. Mice displaying progressively masses in all 10 mammary glands and those that reach 33 week of age are killed and morphologically examined.

Histological examination of the mammary gland at progressive time points in a fashion blind to the treatment reveals the progression of the HER-2/neu oncogenesis in the treated mice. The incidence of atypical hyperplasia (week 10) and the number of carcinoma in situ (week 15) shows the anti-tumor activity induced by oral LF in combination with tumor cell vaccination. Tumor progression is associated with neovascularization and lack of infiltrating CD8+, and to a lesser extent CD4+, lymphocytes evident by histology analysis of animals. The level of vascularization and T cell infiltration in tumors treated with LF reveals the activity of oral LF.

Example 7

Oral Administration of hLF in Combination with a Cancer Vaccine in Patients

Recombinant human lactoferrin is orally administered to human patients in combination with a cancer vaccine to inhibit tumor growth. The cancer vaccine is the HER-2/neu. The following peptides used in this study are HER-2/neu peptides, p369-384, SEQ.ID.NO:5 KIFGSLAFLPES-FDGDPA (Disis et al., 2000), p688-703, SEQ.ID.NO:6 RRLLQETELVEPLTPS (Disis et al., 2000), p971-984, SEQ.ID.NO:7 ELVSEFSRMARDPQ (Disis et al., 2000), p369-377, SEQ.ID.NO:8 KIFGSLAFL (Fisk et al., 1995), p689-697, SEQ.ID.NO:9 RLLQETELV (Peoples et al., 1995), and p971-979, SEQ.ID.NO:10 ELVSEFSRM (Ioannides et al., 1993).

Briefly, rhLF is administered at a dose of 4.5 g per day (3 g in the morning, 1.5 g at night in cycles of 14 days on, 14 days off (maximum 5 cycles) or rhLF 9 g per day (4.5 g bid in cycles of 14 days on, 14 days off (maximum 5 cycles) to patients with metastatic HER-2/neu-overexpressing cancers. The dose is administered orally.

Patients also receive monthly vaccinations with three 15-amino acid HER-2/neu-derived peptides containing within each the putative HLA-A2-binding motifs (Knutson et al., 2001). Five hundred micrograms of each peptide (1.5 microgram total peptide dose) are administered to the same draining lymph node site via two intradermal injections for 6 months.

Tumor size progression is monitored through CT scans and tumor markers where available. CT scans are performed at baseline and after each 8-week period once treatment is initiated. Tumor markers are measured every 4 weeks. Blood samples are collected to measure the mean peptide-specific T-cell precursor frequency to the HLA-A2 peptides. Peptide-specific T cell killing is also evaluated. Plasma, serum and blood cell extract samples are collected to measure circulating IL-18, IL-1, IL-2, and IL-4, IL-5, IL-10, IL-12 and IFN-γ.

Example 8

Effect of rhLF on Mucosal Immunity in Mice

Figure 2:
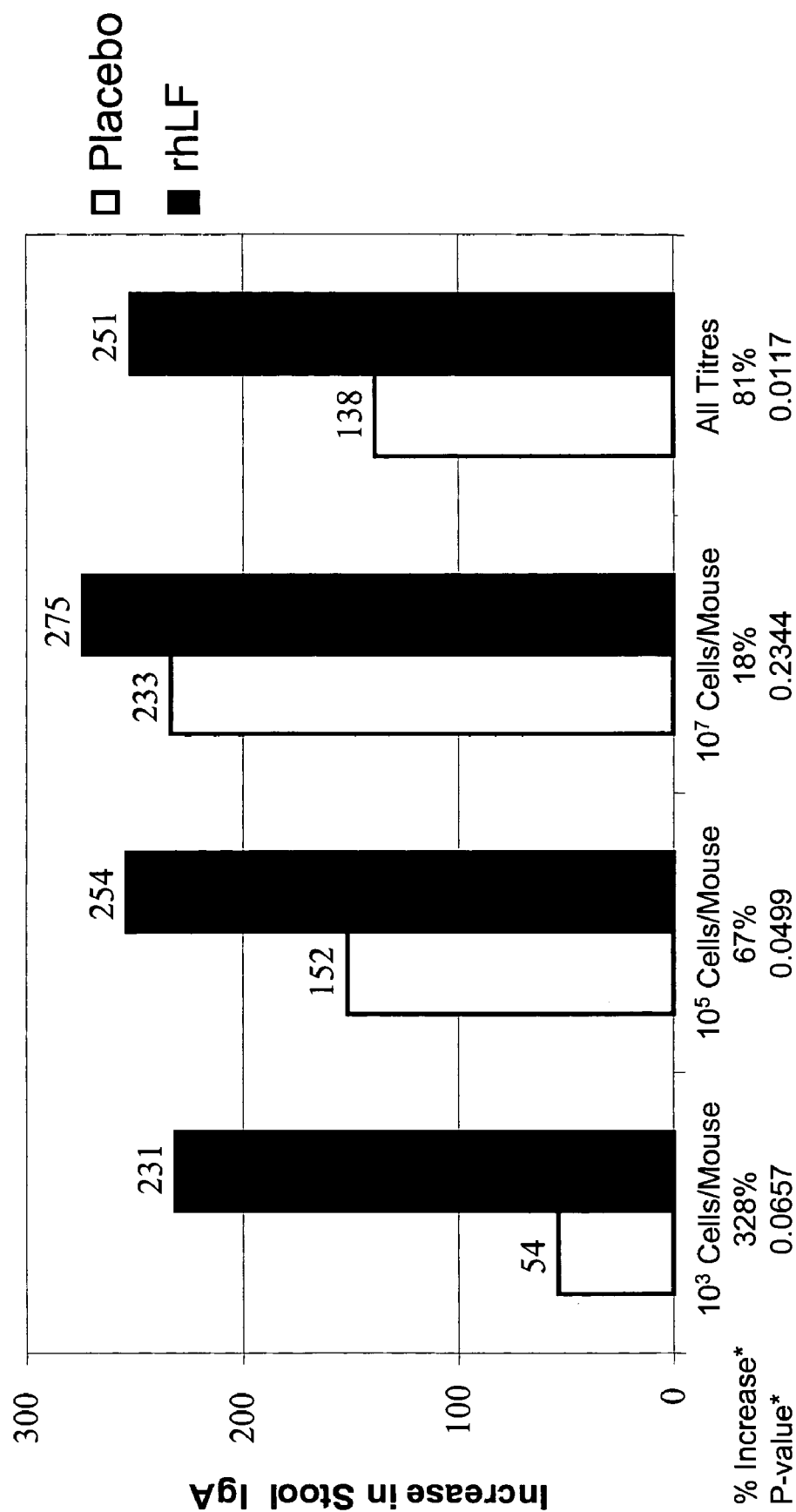
FIG. 2 shows the effect of rhLF on mucosal immunity in mice.

BALBc mice were administered live attenuated S typhimenium (Ty21a) by oral gavage at various doses. Animals also received oral rhLF (65 mg/kg) on the day before and on the day of the Ty21a administration. Stool samples were collected 19 days after Ty21a administration and mucosal immunity evaluated by measuring stool EspA specific sIgA antibodies. Results show that rhLF induces similar immunity with a 10,000 fold lower titre (FIG. 2).

REFERENCES CITED

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 5,629,001
Alfonso M, et al., *J Immunol.* 168:2523-9, 2002.
Amici et al., *Cancer Immunol. Immunother.*, 47:183-90. 1998.
Bezault J et. al., *Cancer Res.* 1994, 54(9):2310-2.
Boggio et al., *J. Exp. Med.*, 1998, 188:589-596
Borrello I M, et al., *Cancer Control* 2002, 9:138-151
Bronte V, *Curr. Gene Ther.* 2001, 1:53-100
Broxmeyer H E. *Blood.* 1983; 61:982-993.
Chang A E, et al., *J Clin. Oncol.* 21:884-90
Curiel T, et al. *J. Clin. Invest.* 2002, 109:311-312.
Damiens E, et al., *Biochim Biophys Acta.* 1998, 1402(3):277-87.
Dhennin-Duthille I, et al., *J Cell Biochem.* 2000, 79(4):583-93.
Disis et al. *Transplantation*, 2000.
Disis et al., *Breast Cancer Res Treat*, 62:245-52, 2000.
Dredge K, et al., *Cancer Immunol. Immunother.* 2002, 51(10):521-31
Dudley M et al., *Science.* 2002, 298(5594):850-4
Erlandsson, *Cancer Genet. Cytogenet,* 104:1-18, 1998.
Fisk et al., *J. Exp. Med.*, 181:2109-17, 1995.
Forni G, et al. *Curr. Opin. Mol. Ther.* 1999, 1:34-8
Gahr M, et al., *J Leukocyte Biol.* 1991;49: 427-33.
Gertig and Hunter, *Semin. Cancer Biol.*, 8(4):285-298, 1997.
Gullick et al., Br. 1991, *J. Cancer,* 63:434.
Horowitz D A, et al., *J Immunol.* 1984; 132: 2370-4.
Horvath et al., *Acta Microbiol Immunol. Hung,* 1999, 46:1-20
Iigo M, et al., *Clin Exp Metastasis.* 1999, 17(1):35-40.
Ioannides et al., *Cell. Immunol.*, 151:225-34, 1993.
Knutson K L et al., *J. Clin. Invest.*, 2001, 107:477.
Knutson K L, *Curr. Opin. Investig. Drugs* 2002, 3:159-64
Kolmel, *J. Neurooncol.*, 38:121-125, 1998.
Kuhara T, et al., *Nutr Cancer.* 2000, 38(2): 192-9.
Machiels J P, et al., 2002, 29:459-502
Magi-Galluzzi et al., *Anal. Quant. Cytol. Histol.*, 20:343-350, 1998.
Mangray and King, *Front Biosci.*, 3:D1148-1160, 1998.
Masuda C, et al. *Jpn J Cancer Res.* 2000, 91(6):582-8.
Mayer, *Radiat Oncol Investig.* 6:281-8, 1998.
Mumby and Walter, *Cell Regul.*, 2:589-598, 1991.
Nagata et al., *J. Immunol.* 1997, 159:1336
Nanni et al., *J. Exp. Med.* 2001, 194:1195.
Natoli et al., *Biochem. Pharmacol.*, 56(8):915-920, 1998.
Ohara, *Acta Oncol.* 37:471-4, 1998.
Pardoll D, *Nature Reviews Immunol.*, 2002, 2:227-238.
Peoples et al., *Proc. Natl. Aca. Sci.*, 92:6547-511995, 1995.
Rovero et al., *J. immuno.*, 2000, 165:5133-5142
Sabel M S, et al., *Am. J. Clin. Dermatol.* 2002, 3:609-16
Shau H, et al., *J Leukocyte Biol.* 1992; 51:343-9.
Solyanik et al., *Cell Prolif.,* 28:263-278, 1995.
Spik G, et al., *Adv Exp Med Biol.* 1994; 357:13-9.
Stokke et al., *Cell Prolif.*, 30(5):197-218, 1997.
Tanaka T, et al. *Jpn J Cancer Res.* 2000, 91(1):25-33.
Tsuda H, et al., *Biofactors.* 2000; 12(1-4):83-8.
Ushida Y, et al. *Jpn J Cancer Res.* 1999, 90(3):262-7.
Vaiashampayan et.al., *Clin. Cancer Res.* 2002, 8:3696-701
Wang W P, et al., *Jpn J Cancer Res.* 2000, 91(10):1022-7.
Yoo Y C, et al., *Adv Exp Med Biol.* 1998, 443:285-91.
Yoo Y C, et al., *Jpn J Cancer Res.* 1997, 88(2):184-90.

Although the present invention and its advantages have been described in detail, it should be understood that various changes, substitutions and alterations can be made herein without departing from the spirit and scope of the invention as defined by the appended description. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended descriptions are intended to include within their scope such processes, machines, manufacture, compositions of matter, means, methods, or steps.

What is claimed is:

1. A method of treating cancer comprising the step of administering to a subject a cancer immunotherapy and an adjuvant, wherein said adjuvant is a human lactoferrin composition that is administered orally for gastrointestinal delivery in an amount sufficient to provide an improvement in the cancer in said subject.

2. The method of claim 1, wherein the cancer is breast cancer.

3. The method of claim 1, wherein the cancer immunotherapy comprises DNA-based immunotherapy that comprises administration of a nucleic acid encoding a cancer antigen.

4. The method of claim 1, wherein said lactoferrin composition is dispersed in a pharmaceutically acceptable carrier.

* * * * *

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
cgcaagcttc atcatggagc tggc                                        24

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
cggaattcgg gctggctctc tgctc                                       25

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
cgcaagcttc atggagctgg c                                           21

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
atgaattctt tccgcatcgt gtacttcttc cgg                              33

<210> SEQ ID NO 5
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 5

Lys Ile Phe Gly Ser Leu Ala Phe Leu Pro Glu Ser Phe Asp Gly Asp
1               5                   10                  15

Pro Ala

<210> SEQ ID NO 6
<211> LENGTH: 16
```

```
<212> TYPE: PRT
<213> ORGANISM: Artificial Sequence
<220> FEATURE:
<223> OTHER INFORMATION: Synthetic Peptide

<400> SEQUENCE: 6

Arg Arg Leu Leu Gln Glu Thr Glu Leu Val Glu Pro Leu Thr Pro Ser
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 7

Glu Leu Val Ser Glu Phe Ser Arg Met Ala Arg Asp Pro Gln
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Lys Ile Phe Gly Ser Leu Ala Phe Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 9

Arg Leu Leu Gln Glu Thr Glu Leu Val
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 10

Glu Leu Val Ser Glu Phe Ser Arg Met
1               5
```